(12) United States Patent
Rahamim et al.

(10) Patent No.: US 9,445,747 B2
(45) Date of Patent: Sep. 20, 2016

(54) APNEA DETECTOR AND SYSTEM

(75) Inventors: Shaked Rahamim, Moshav Netua (IL); Ori Elyada, Hod Hasharon (IL)

(73) Assignee: DIAPERTECH LTD, Reut (IL)

( * ) Notice: Subject to any disclaimer, the term of this patent is extended or adjusted under 35 U.S.C. 154(b) by 812 days.

(21) Appl. No.: 13/608,699

(22) Filed: Sep. 10, 2012

(65) Prior Publication Data

US 2013/0123654 A1 May 16, 2013

Related U.S. Application Data

(63) Continuation of application No. 12/762,563, filed on Apr. 19, 2010, now abandoned, which is a continuation-in-part of application No. PCT/IL2008/001349, filed on Oct. 12, 2008.

(30) Foreign Application Priority Data

Oct. 18, 2007 (IL) .......................... 186768

(51) Int. Cl.
*A61B 5/08* (2006.01)
*A61B 5/113* (2006.01)
*A61B 5/00* (2006.01)
*A61F 5/56* (2006.01)

(52) U.S. Cl.
CPC ........... *A61B 5/0826* (2013.01); *A61B 5/0026* (2013.01); *A61B 5/113* (2013.01); *A61B 5/1135* (2013.01); *A61B 5/4818* (2013.01); *A61B 5/6804* (2013.01); *A61B 5/6808* (2013.01); *A61B 5/7282* (2013.01); *A61B 5/742* (2013.01); *A61B 5/7405* (2013.01); *A61B 5/746* (2013.01); *A61F 5/56* (2013.01); *A61B 2562/0261* (2013.01)

(58) Field of Classification Search
CPC A61B 5/1135; A61B 5/4818; A61B 5/6804; A61B 5/0026; A61B 5/746; A61B 5/113; A61B 5/6808; A61B 5/7282; A61B 5/7405; A61B 5/742; A61B 5/0826; A61F 5/56
See application file for complete search history.

(56) References Cited

U.S. PATENT DOCUMENTS 4,433,693 A * 2/1984 Hochstein ............ A61B 5/0002
600/534
5,295,490 A * 3/1994 Dodakian ............ A61B 5/1135
600/534

(Continued)

OTHER PUBLICATIONS

Dhillon H S and Singhal H: "Novel Electronics Hardware for Continuous Time Respiration Signal Monitoring and Sleep Apnea Detection" Proc. Int. Conf. on Advances in Electronics and Comm. Tech. (ICAECT), Dec. 2006, pp. 1-4, XP002515483.*

(Continued)

*Primary Examiner* — Navin Natnithithadha
*Assistant Examiner* — Eric Messersmith
(74) *Attorney, Agent, or Firm* — Mark M. Friedman

(57) ABSTRACT

An apnea detector is disclosed. A detector unit in communication with a capacitive type sensor is adapted to receive an electrical signal which is indicative of variable capacitance resulting from movement of a subject and to emit an alert signal when the received electrical signal is indicative of symptoms of apnea. In one embodiment, a detector unit is in communication with a curvature sensor adapted to detect a variable curvature of a subject body surface resulting from breathing patterns of a subject. The detector unit is attached to an article of clothing of the subject.

9 Claims, 28 Drawing Sheets

(56) References Cited

U.S. PATENT DOCUMENTS

| | | | | |
|---|---|---|---|---|
| 5,454,376 A * | 10/1995 | Stephens | A61B 5/6805 | 600/534 |
| 5,749,365 A * | 5/1998 | Magill | A61B 5/0008 | 128/903 |
| 6,105,440 A * | 8/2000 | Lawless | 73/863.21 | |
| 6,267,730 B1 * | 7/2001 | Pacunas | A61B 5/113 | 600/529 |
| 7,800,505 B2 * | 9/2010 | Pietersen | A61B 5/0002 | 340/517 |
| 2002/0057202 A1 * | 5/2002 | Luzon | A61B 5/0816 | 340/573.1 |
| 2005/0054941 A1 * | 3/2005 | Ting | A61B 5/0408 | 600/529 |
| 2005/0245839 A1 * | 11/2005 | Stivoric | G06F 19/3418 | 600/549 |
| 2006/0258916 A1 * | 11/2006 | Pietersen | A61B 5/0002 | 600/301 |
| 2007/0085690 A1 * | 4/2007 | Tran | 340/573.1 | |
| 2008/0000304 A1 * | 1/2008 | Nagle | A61B 5/1135 | 73/780 |
| 2008/0064964 A1 * | 3/2008 | Nagata | A61B 5/0205 | 600/484 |
| 2008/0252445 A1 * | 10/2008 | Kolen | 340/539.16 | |
| 2008/0275328 A1 * | 11/2008 | Jones | A61B 5/024 | 600/407 |
| 2008/0309765 A1 * | 12/2008 | Dayan | H04N 7/185 | 348/158 |
| 2010/0283485 A1 * | 11/2010 | Valisuo | G01D 5/24 | 324/663 |

OTHER PUBLICATIONS

Chang et al., "Capacitive pressure sensors with stainless steel diaphragm and substrate," J. Micromech. Microeng. 14 (2004) 612-618.*

* cited by examiner

APNEA DETECTOR AND SYSTEM

CROSS-REFERENCE TO RELATED APPLICATIONS

This patent application is a continuation of U.S. Ser. No. 12/762,563 filed on Apr. 19, 2010 which is a continuation-in-part of PCT/IL2008/001349 filed on Oct. 12, 2008 and published as WO 2009/050702, and claims priority to Israel Patent Application 186768 filed on Oct. 18, 2007. Each of the aforementioned patent applications including U.S. Ser. No. 12/762,563 and PCT/IL2008/001349 is hereby incorporated by reference in their entirety.

FIELD OF THE INVENTION

The present invention relates to the field of monitoring systems. More particularly, the invention relates to an apnea detector that is embedded in a diaper or otherwise attached to an article of clothing.

BACKGROUND OF THE INVENTION

A constant concern of parents of a sleeping infant, generally less than one year old, is the onset of sudden infant death syndrome (SIDS). Parents usually inspect the breathing patterns of their infant several times during a nighttime period to determine whether there are signs of the onset of SIDS.

It would be desirable to provide a reliable and inexpensive detector for infant apnea, which is one of the most recognizable signs of SIDS. An infant who has ceased to breathe can be revived only if a parent, who has been trained to provide first aid care, is immediately alerted to such a life threatening condition.

Some adults are also prone to sleep apnea due to various medical causes. It would be desirable to provide a reliable and ergonomic detector for monitoring sleep apnea and for stimulating the subject to awake when sleep apnea occurs.

Three types of prior art apnea detectors are known:
1) An apnea detector such as disclosed in U.S. Pat. No. 5,271,412, WO 2005/074379, U.S. Pat. No. 4,146,885 and U.S. Pat. No. 5,684,460 is placed underneath the mattress of the infant, and a parent is immediately alerted when apnea is detected. It is needless to say that this type of detector is unable to detect apnea when the infant is not sleeping, such as when playing, or when not sleeping on his mattress. This type of detector is also relatively expensive to manufacture. Another disadvantage of this type of apnea detector is that the mattress is interposed between the infant and the detector that senses the breathing pattern of the infant. The received signal is therefore attenuated by the mattress material, and its transmission is also delayed due to the gradual relaxation of the spongy mattress material, causing a life threatening delay during an apnea event.
2) One type of apnea detector, such as disclosed in U.S. Pat. No. 5,454,376 or U.S. Pat. No. 5,241,300, involves a wearing apparel having an elastic belt that extends about the chest or abdomen of the infant. A strain gauge is secured to the belt and detects breathing movement through the expansion and contraction of the chest wall. Such a detector is uncomfortable or even dangerous to the wearer, particularly during the nighttime hours, due to the pressure exerted by the elastic belt, and therefore cannot be used during an entire 24-hour period. Apnea cannot be detected when the wearing apparel is being laundered. Additional disadvantages of this type of detector are that the detector is not suitable for different sized infants and that it is not capable for detecting moisture in a diaper.

U.S. Pat. Nos. 5,295,490, 4,696,307, 4,989,612, 5,107,855, and 5,400,012 disclose a variation of this type of apnea detector in which belt means encircling a portion of the body of a patient expands and contracts in response to respiration of the patient. This belt means poses a risk of entanglement and suffocation to the monitored infant.

3) Another type of apnea detector, such as disclosed in GB 2261290, U.S. Pat. No. 3,782,368, U.S. Pat. No. 5,684,460, U.S. Pat. No. 6,267,730 and WO 2005/011491, comprises a piezoelectric element for detecting deflections caused by respiratory and heart functions. A piezoelectric element is relatively expensive, and therefore is not disposable. Also, a piezoelectric element is fragile, and may be easily broken by the infant or by his parents, therefore constituting an unreliable detector.

Other apnea detectors are disclosed in WO 02/34133, JP 9,187,431, U.S. Pat. Nos. 5,993,397 and 6,267,730.

U.S. Pat. Nos. 5,838,240 and 6,677,859 disclose the use of a capacitive sensor for detecting moisture, such as in a diaper. A capacitive sensor has not been used heretofore to detect sleep apnea.

It is an object of the present invention to provide a reliable and inexpensive detector for infant apnea.

It is an additional object of the present invention to provide an infant apnea detector and system, which are operable throughout a 24-hour period, even when the infant is awake and not in a prone position.

It is an additional object of the present invention to provide an infant apnea sensor that is embedded within a diaper.

It is an additional object of the present invention to provide an infant apnea sensor that is disposable.

It is an additional object of the present invention to provide an infant apnea detector that is comfortable and safe to the infant.

It is an additional object of the present invention to provide an infant apnea detector that is difficult to be removed by the infant from the diaper to which it is attached.

It is an additional object of the present invention to provide an infant apnea detector and system that are also capable of detecting wetness and other infant related parameters of interest.

It is yet an additional object of the present invention to provide an infant apnea detector system that can instantly alert a parent upon detection of apnea.

It is yet an additional object of the present invention to provide an infant apnea detector system that does not expose the infant to close-proximity radio frequency (RF) radiation.

It is yet an additional object of the present invention to provide an infant apnea detector and sensor that are not in direct contact with the body of the infant.

Other objects and advantages of the invention will become apparent as the description proceeds.

SUMMARY OF THE INVENTION

The present invention provides an apnea detector which comprises a capacitive type sensor adapted to detect a variable capacitance resulting from movement of a subject, such as the breathing patterns of the subject, and a detector unit in communication with said sensor for receiving an electrical signal from said capacitive type sensor which is indicative of said variable capacitance and for emitting an alert signal, such as by alerting an attendant, when said received electrical signal is indicative of symptoms of apnea, said detector unit being attached to an article of clothing of the subject, such as a diaper.

As referred to herein, a "subject" is one who is being monitored by means of an apnea detector, e.g. an adult subject or an infant subject.

In one aspect, the detector unit is releasably attached to an article of clothing of the subject.

In one aspect, the capacitive type sensor is adapted to detect a variable capacitance between two serially connected capacitor plates and a body surface of the subject.

In one aspect, the subject is an infant and the detector unit is attached to a diaper.

In one aspect, the capacitive type sensor comprises a conductive surface constituting a capacitor plate which is applied to a suitable diaper surface, e.g. an inner face of a diaper outer layer, such as being attached thereto, said sensor adapted to detect a variable capacitance between said plate and a body surface of the subject.

The variable capacitance is dependent upon an instantaneous capacitance of diaper absorbent core material and an air gap interposed between the plate and the subject body surface.

In one aspect, the conductive surface is applied to a suitable diaper surface by conductive ink or hot foil stamping.

In one aspect, the conductive surface is attached to a suitable diaper surface.

In one aspect, the sensor is capacitively coupled to the detector unit.

In one aspect, the detector unit is in communication with said sensor by means of electric contacts.

The detector unit preferably comprises a microcontroller, an enunciator in communication with said microcontroller for emitting acoustical information when symptoms of apnea are detected, a battery, a flexible or rigid printed circuit board, means for communicating with the capacitive type sensor, and a recessed button for activating or deactivating said microcontroller or for silencing an enunciated alarm signal.

The microcontroller receives and processes electrical signals from the sensor, and determines by means of a firmware algorithm whether symptoms of apnea are being exhibited. Subject related parameters are stored in an event log module which is associated with the microcontroller. Data is exchanged with the microcontroller by means of an external data interface.

In one aspect, the means for communicating with the capacitive type sensor comprises a coupling pad externally attached to a detector unit casing underside and electrically connected with the printed circuit board.

In one aspect, the detector unit comprises two or more coupling pads, for communicating with two or more spaced capacitive type sensors.

In one aspect, the detector unit further comprises an optical indicator in communication with the microcontroller for visually alerting an attendant when symptoms of apnea are detected or for indicating a detector status.

In one aspect, the detector unit is also in communication with one or more additional sensors adapted to detect infant related parameters of interest, which are selected from the group of urine detection, feces detection, subject heartbeat detection, ambient temperature and humidity, illumination level, infant locating transponder, body temperature, body activity, oxygen saturation of arterial blood,. and sleeping orientation of infant.

In one aspect, the capacitive type sensor comprises two spaced conductive surfaces constituting capacitor plates which are applied to a substrate, said substrate being embedded within diaper absorbent core material such that said two spaced conductive surfaces face each other, said sensor adapted to detect a variable capacitance between said two spaced conductive surfaces.

The present invention is also directed to an apnea detector which comprises a curvature sensor adapted to detect a variable curvature of a subject body surface resulting from breathing patterns of a subject, and a detector unit in communication with said sensor for receiving an electrical signal from said curvature sensor which is indicative of said variable curvature and for emitting an alert signal when said received electrical signal is indicative of symptoms of apnea, said detector unit being attached to an article of clothing.

The curvature sensor is selected from the group of a resistive strain gauge, a flexion sensor, a piezoelectric transducer, a sensor made of piezoresistive materials, a fiber optic element for measuring bending or stretching by means of optical refraction, diffraction, scattering, transmissivity, or polarization, and a force-sensitive resistor.

In one aspect, the detector unit is releasably attached to an article of clothing of the subject.

In one aspect, the subject is an infant and the detector unit is attached to a diaper.

In one aspect, the detector unit comprises a microcontroller, an enunciator in communication with said microcontroller for emitting acoustical information when symptoms of apnea are detected, a battery, a flexible or rigid printed circuit board, means for communicating with the curvature sensor, and a recessed button for activating or deactivating said microcontroller or for silencing an enunciated alarm signal.

The present invention is also directed to a subject monitoring system which comprises a detector unit for detecting one or more subject related parameters of interest and for emitting acoustical information after determining that a subject related parameter of interest has a predetermined status, and a stationary unit disposed within an audible range of said detector unit for receiving said emitted acoustical information.

The stationary unit preferably comprises a microphone, a microcontroller, means for filtering noise and tones that have a frequency outside a predetermined frequency band and for transmitting filtered signals to said stationary unit microcontroller, and means for generating an alert signal when said stationary unit microcontroller determines that the filtered signals are indicative of a predetermined audio signal emitted by the detector unit.

In one aspect, the predetermined audio signal emitted by the detector unit is an acoustical signature.

In one aspect, the alert signal generated by the stationary unit is a high-volume warning signal.

In one aspect, the alert signal is adapted to alert an authorized attendant that a subject related parameter of interest has a predetermined status.

In one aspect, the stationary unit further comprises a transceiver, the alert signal being a wireless signal transmitted by said stationary unit transceiver.

In one aspect, the stationary unit comprises means for receiving, amplifying and emitting acoustical information enunciated by the subject.

In one aspect, the stationary unit comprises a display in communication with the stationary unit microcontroller for outputting textual information indicative of the predetermined subject status.

In one aspect, the stationary unit comprises one or more optical indicators in communication with the stationary unit microcontroller, illumination of each of said indicators being indicative of generation of an alarm signal.

In one aspect, the stationary unit further comprises an external data interface for exchanging data with the stationary unit microcontroller.

In one embodiment, the system further comprises a portable unit in communication with the stationary unit transceiver via a communication network, said portable unit being accessible to the authorized attendant and adapted to enunciate acoustical information emitted by the stationary unit.

In one aspect, a subject related parameter of interest detected by the detector unit is a characteristic breathing pattern value (CBPV).

In one aspect, a capacitive type sensor in communication with the detector unit transmits an electrical signal thereto which is indicative of a variable capacitance CBPV.

In one aspect, the capacitive type sensor comprises a conductive surface applied to a suitable diaper surface, said sensor adapted to detect a variable capacitance between said surface and a body surface of an infant.

In one aspect, a curvature sensor in communication with the detector unit transmits an electrical signal thereto which is indicative of a variable curvature CBPV representing a variable curvature of a subject body surface.

In one embodiment, the system further comprises an override unit in communication with the stationary unit transceiver and connected to a set-top box of a home entertainment system, said override unit adapted to interrupt the display of a program on said home entertainment system and to display a predetermined video frame thereon.

Some embodiments relate to an apnea detector, comprising a capacitive type sensor adapted to detect a variable capacitance resulting from movement of a subject, and a detector unit in communication with said sensor for receiving an electrical signal from said capacitive type sensor which is indicative of said variable capacitance and for emitting an alert signal when said received electrical signal is indicative of symptoms of apnea, said detector unit being attached to an article of clothing of the subject.

In some embodiments, the capacitive type sensor is adapted to detect a variable capacitance resulting from breathing patterns of the subject.

In some embodiments, the detector unit is releasably attached to an article of clothing of the subject.

In some embodiments, the subject is an infant and the detector unit is attached to a diaper.

In some embodiments, the capacitive type sensor comprises a conductive surface constituting a capacitor plate which is applied to a suitable diaper surface, said sensor adapted to detect a variable capacitance between said plate and a body surface of the infant.

In some embodiments, the variable capacitance is dependent upon an instantaneous capacitance of diaper absorbent core material and an air gap interposed between the plate and the infant body surface.

In some embodiments, the suitable diaper surface is an inner face of a diaper outer layer.

In some embodiments, the conductive surface is applied to a suitable diaper surface by conductive ink or hot foil stamping.

In some embodiments, the conductive surface is attached to a suitable diaper surface.

In some embodiments, the sensor is capacitively coupled to the detector unit.

In some embodiments wherein the detector unit is in communication with said sensor by means of electric contacts.

In some embodiments, the detector unit comprises a microcontroller, an enunciator in communication with said microcontroller for emitting acoustical information when symptoms of apnea are detected, a battery, a flexible or rigid printed circuit board, means for communicating with the capacitive type sensor, and a recessed button for activating or deactivating said microcontroller or for silencing an enunciated alarm signal.

In some embodiments, the means for communicating with the capacitive type sensor comprises a coupling pad externally attached to a detector unit casing underside and electrically connected with the printed circuit board.

In some embodiments, the detector unit comprises two or more coupling pads, for communicating with two or more spaced capacitive type sensors.

In some embodiments, the detector unit further comprises an optical indicator in communication with the microcontroller for visually alerting an attendant when symptoms of apnea are detected or for indicating a detector status.

In some embodiments, the detector unit is also in communication with one or more additional sensors adapted to detect subject related parameters of interest.

In some embodiments, wherein the subject related parameters of interest are selected from the group of urine detection, feces detection, heartbeat detection, ambient temperature and humidity, illumination level, subject locating transponder, body temperature, body activity, oxygen saturation of arterial blood, and sleeping orientation of infant.

In some embodiments, the capacitive type sensor is adapted to detect a variable capacitance between two serially connected capacitor plates and a body surface of the subject.

In some embodiments, the capacitive type sensor comprises two spaced conductive surfaces constituting capacitor plates which are applied to a substrate, said substrate being embedded within diaper absorbent core material such that said two spaced conductive surfaces face each other, said sensor adapted to detect a variable capacitance between said two spaced conductive surfaces.

Some embodiments of the present invention provide an apnea detector, comprising a curvature sensor adapted to detect a variable curvature of a subject body surface resulting from breathing patterns of a subject, and a detector unit in communication with said sensor for receiving an electrical signal from said curvature sensor which is indicative of said variable curvature and for emitting an alert signal when said received electrical signal is indicative of symptoms of apnea, said detector unit being attached to an article of clothing.

In some embodiments, the detector unit is releasably attached to an article of clothing of the subject.

In some embodiments, the subject is an infant and the detector unit is attached to a diaper.

In some embodiments, the curvature sensor is selected from the group of a resistive strain gauge, a flexion sensor, a piezoelectric transducer, a sensor made of piezoresistive materials, a fiber optic element for measuring bending or stretching by means of optical refraction, diffraction, scattering, transmissivity, or polarization, and a force-sensitive resistor.

Some embodiments of the present invention relate to a monitoring system, comprising a detector unit for detecting one or more subject related parameters of interest and for emitting acoustical information after determining that a subject related parameter of interest has a predetermined status, and a stationary unit disposed within an audible range of said detector unit for receiving said emitted acoustical information.

Some embodiments of the present invention relate to a monitoring system, comprising (a) detector unit configured to detect a presence of a symptom of apnea; (b) an audio speaker for emitting an audio alert signal (i.e. for example, having predetermined characteristics) contingent upon the detected presence of a symptom of apnea; (c) a microphone in audible range of the audio speaker configured to detect sound and to generate an electrical signal descriptive of the detected sound; and (d) electrical circuitry (i.e. including any combination of digital or analog electrical hardware and/or software/executable computer code—for example, including one or more microprocessors, volatile and/or non-volatile memory, and/or executable code stored in memory) configured to analyze the electrical signal descriptive of the detected sound and to determine if the electrical signal descriptive of the detected sound matches the audio alert signal; and (e) an alert signal-emitting unit (e.g. including a speaker or visual display or digital computer configured to sent an electronic communication) configured, in response to the results of the analysis by the electrical circuitry, and contingent upon a positive matching (i.e. a determination that the electrical signal descriptive of the detected sound from the microphone does match the sound characteristics of the audio alert signal), to emit one or more additional alert signals.

In one example, the additional alert signal is an additional audio alert signal. In another example, the additional alert signal may be visual alert signal. In yet another example, the additional alert signal may be provided by an electronic communication such as an email, a text message (e.g. an SMS), or a communication via a packet switched and/or internet network. In yet another example, the additional alert signal may be a radio signal or infra-red data communication.

Some embodiments of the present invention relate to a monitoring system, comprising (a) detector unit configured to detect a indication of condition requiring care by a parent, guardian or medical professional; (b) an audio speaker for emitting an audio alert signal (i.e. for example, having predetermined characteristics) contingent upon the detected indication of the condition requiring care by a parent, guardian or medical professional; (c) a microphone in audible range of the audio speaker configured to detect sound and to generate an electrical signal descriptive of the detected sound; and (d) electrical circuitry (i.e. including any combination of digital or analog electrical hardware and/or software/executable computer code—for example, including one or more microprocessors, volatile and/or non-volatile memory, and/or executable code stored in memory) configured to analyze the electrical signal descriptive of the detected sound and to determine if the electrical signal descriptive of the detected sound matches the audio alert signal; and (e) an alert signal-emitting unit (e.g. including a speaker or visual display or digital computer configured to sent an electronic communication) configured, in response to the results of the analysis by the electrical circuitry, and contingent upon a positive matching (i.e. a determination that the electrical signal descriptive of the detected sound from the microphone does match the sound characteristics of the audio alert signal), to emit one or more additional alert signals.

Examples of conditions requiring care by a parent, guardian or medical professional include a presence or urine or feces, apnea and an abnormal body temperature.

In some embodiments, the stationary unit comprises a microphone, a microcontroller, means for filtering noise and tones that have a frequency outside a predetermined frequency band and for transmitting filtered signals to said stationary unit microcontroller, and means for generating an alert signal when said stationary unit microcontroller determines that the filtered signals are indicative of a predetermined audio signal emitted by the detector unit.

In some embodiments, the predetermined audio signal emitted by the detector unit is an acoustical signature.

In some embodiments, the alert signal generated by the stationary unit is a high-volume warning signal.

In some embodiments, the stationary unit further comprises a transceiver, the alert signal being a wireless signal transmitted by said stationary unit transceiver.

In some embodiments, the stationary unit comprises means for receiving, amplifying and emitting acoustical information enunciated by the subject.

In some embodiments, the stationary unit comprises a display in communication with the stationary unit microcontroller for outputting textual information indicative of the predetermined subject status.

In some embodiments, the stationary unit comprises one or more optical indicators in communication with the stationary unit microcontroller, illumination of each of said indicators being indicative of generation of an alarm signal.

In some embodiments, the stationary unit further comprises an external data interface for exchanging data with the stationary unit microcontroller.

In some embodiments, the monitoring system further comprises a portable unit in communication with the stationary unit transceiver via a communication network, said portable unit being accessible to the authorized attendant and adapted to enunciate acoustical information emitted by the stationary unit.

In some embodiments, a subject related parameter of interest detected by the detector unit is a characteristic breathing pattern value (CBPV).

In some embodiments, a capacitive type sensor in communication with the detector unit transmits an electrical signal thereto which is indicative of a variable capacitance CBPV.

In some embodiments, the capacitive type sensor comprises a conductive surface applied to a suitable diaper surface, said sensor adapted to detect a variable capacitance between said surface and a body surface of the infant.

In some embodiments, a curvature sensor in communication with the detector unit transmits an electrical signal thereto which is indicative of a variable curvature CBPV representing a variable curvature of a subject body surface.

In some embodiments, the system comprises an override unit in communication with the stationary unit transceiver and connected to a set-top box of a home entertainment system, said override unit adapted to interrupt the display of a program on said home entertainment system.

In some embodiments, the override unit is adapted to display a predetermined video frame on, or to enunciate voice information by means of, the home entertainment system.

In some embodiments, the alert signal is adapted to alert an authorized attendant that a subject related parameter of interest has a predetermined status.

DETAILED DESCRIPTION OF PREFERRED EMBODIMENTS

The present invention is a novel detector and monitoring system for apnea, and particularly for infant apnea. A detector unit, which is attached to a clothing article of the subject, is in communication with a sensor which may be ultra-thin, e.g. having a thickness of less than 1 mm. Due to its thin size and cost-effective manufacturing methods, such as being printed by conductive ink, hot foil stamping, conductive polymer tape, and vacuum metallization, the sensor is of low cost and can therefore be sold as a disposable product. The detector unit is integrated with a system, which will be described hereinafter, for instantly alerting an attendant once apnea is detected. Even though the apnea detector is in constant use, the subject is generally not exposed to close-proximity radio frequency radiation.

When the subject is an infant, a detector unit is embedded in, or otherwise attached to, a diaper, and due to its ergonomic configuration by which substantially no discomfort is caused to the infant, the detector unit may be in constant use throughout a 24-hour period, even when the infant is awake and not in a prone position. Since the detector is adapted to detect the breathing patterns of an infant who is distant from his bed or home, the onset of apnea conditions in addition to sudden infant death syndrome (SIDS), such as suffocation, can be advantageously determined.

FIGS. 1-10 illustrate one embodiment of the invention wherein the sensor is a capacitive type sensor which is adapted to measure a variable capacitance, for example between a plate of the sensor and a body surface of the infant. As the infant inhales and exhales, the thickness of an air gap between the diaper and the body surface of the infant periodically changes, and therefore the sensed capacitance correspondingly changes, indicating that the infant has a normal breathing pattern.

Figure 1:
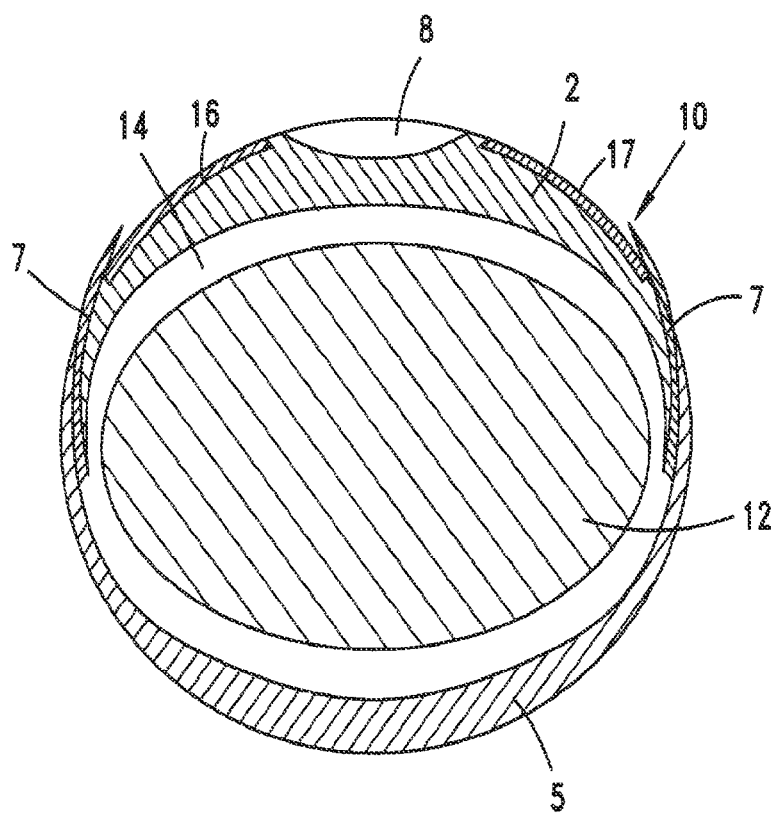
FIG. 1 is a schematic cross sectional view of a diaper protectively attached to an infant body and having a pocket in which a detector unit is retained.

As schematically shown in FIG. 1, diaper 10 comprised of a front section 2 and a rear section 5 is formed with a pocket 8 in which the detector is retained. When diaper 10 is protectively attached to infant body 12, the internal organs of which are not illustrated, front section 2 and rear section 5 of diaper 10 are connected by means of adhesive strips 7 and variable air gap 14 exists between diaper 10 and infant body 12. A change in the thickness of air gap 14 is generally caused by the expansion and contraction of the chest wall, and is also caused by the compression of front section 2 of diaper 10. Sensors 16 and 17 retained in front section 2 detect the expansion and contraction of the chest wall.

Figure 2:
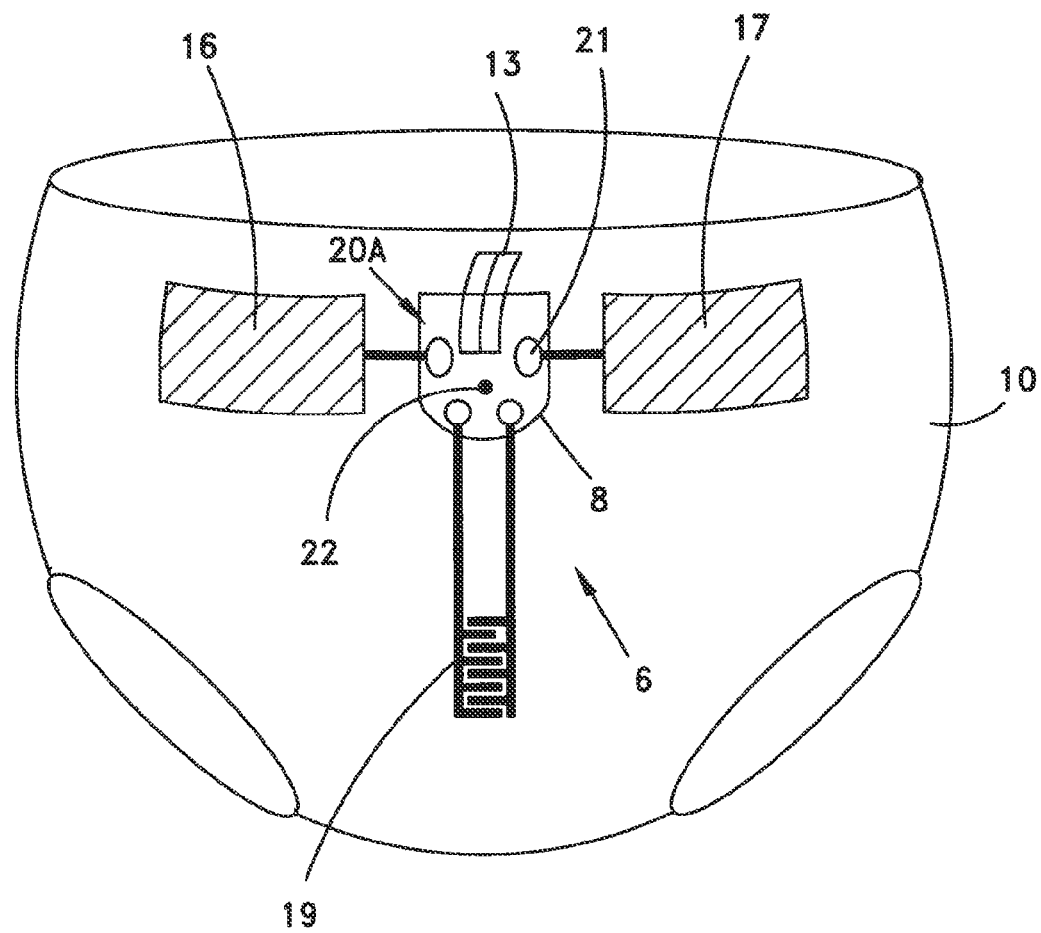
FIG. 2 is a schematic illustration of a detector comprising capacitive type sensors as it is attached to a diaper.

FIG. 2 schematically illustrates a detector generally designated by numeral 6, which comprises apnea detector unit 20A and sensors 16 and 17. Detector unit 20A is retained within pocket 8 of diaper 10 and secured thereto by means of adhesive tab 13. Apnea detector unit 20A is interposed between, and in electrical communication with, two conductive surfaces 16 and 17 constituting capacitor plates, which are printed preferably, but not limitatively, by conductive ink or hot foil stamping, as well known to those skilled in the art. Detector unit 20A may also be in communication with one or more additional sensors 19 that are adapted to detect infant related parameters of interest, such as urine detection, feces detection, infant heartbeat detection, ambient temperature and humidity, illumination level, body temperature, body activity, infant locating transponder, and sleeping orientation of infant. Detector unit 20A may also be in communication with an electronic device, such as an audio monitoring device, and may be provided with means for logging infant activity events. Plates 16 and 17, additional sensors 19, and monitoring equipment are connected to detector 20A by means of corresponding electrical contacts 21 provided in the casing of detector 20A, or, alternatively by means of capacitive coupling through a layer of diaper 10, as will be described hereinbelow. Pocket 8 is preferably formed with one or more holes 22. A hole 22 may be used, for example, to enhance acoustic conductance of a beeper, to facilitate access to a deactivation button, or to improve the viewability of light emitting diode (LED) indicators.

Figure 3:
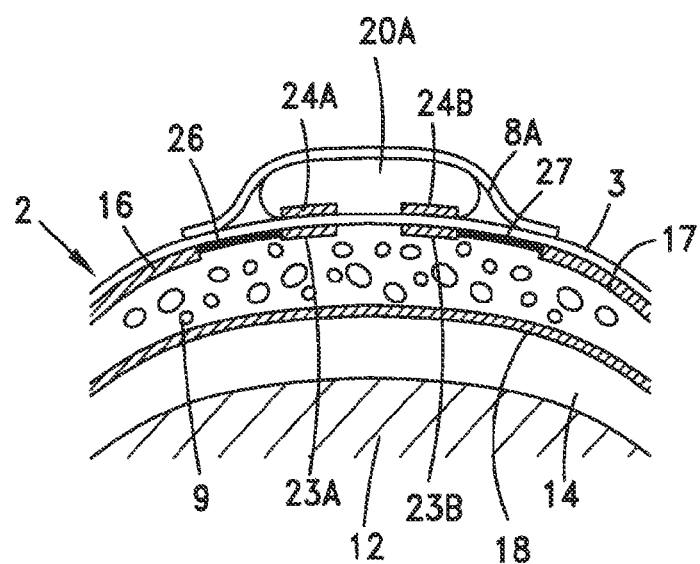
FIG. 3 is a schematic cross sectional view of a front section of a diaper provided with the detector of FIG. 2, according to one embodiment of the invention.

FIG. 3 illustrates front section 2 of a diaper, which comprises outer layer 3, absorbent core 9, and inner layer 18, showing the connection in magnified cross sectional view between plates 16 and 17 and detector unit 20A. Detector unit 20A is placed within pocket 8A, which is welded or bonded to the exterior face of the waterproof outer layer 3 of the diaper. Plates 16 and 17, which are printed on, or attached to, the inner face of outer layer 3 and in contact with absorbent core 9 of the diaper, are capacitively coupled to detector unit 20A by means of coupling pads 23A-B printed on the inner face of diaper outer layer 3 (hereinafter "diaper side coupling pads") and coupling pads 24-B attached to the casing of detector unit 20A (hereinafter "detector side coupling pads"). Conductor 26 connects plate 16 and diaper side coupling pad 23A, and conductor 27 connects plate 17 and diaper side coupling pad 23B.

Figure 4A:
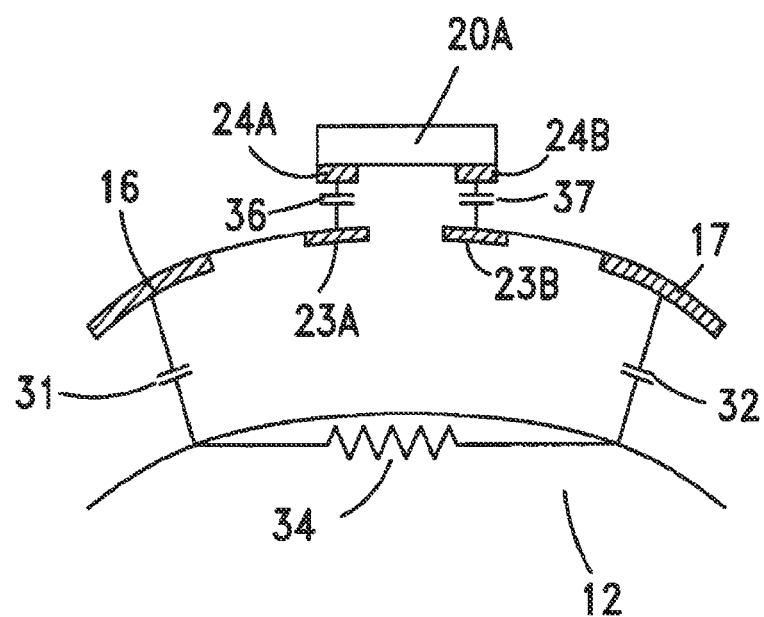
FIG. 4A is a schematic illustration showing the electrical equivalent of each component of the detector of FIG. 3, including the contribution of an infant body.
Figure 4B:
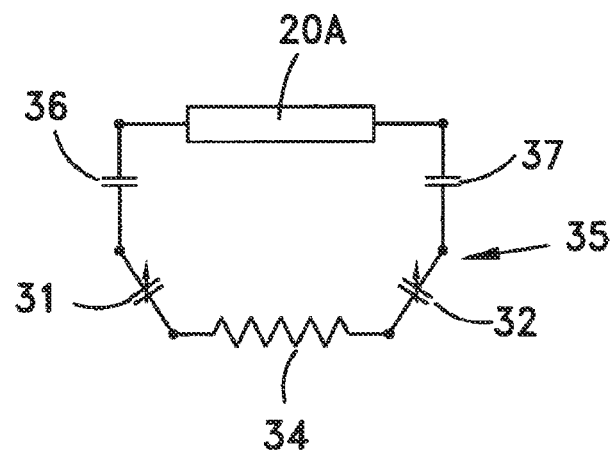
FIG. 4B is an electrical circuit corresponding to FIG. 4A.

FIGS. 4A-B schematically illustrate the electrical equivalent of the circuit 35 defined by the apparatus of this embodiment. As shown, capacitance 31 and capacitance 32 are the variable capacitances between plates 16 and 17, respectively, and infant body 12, wherein the variable capacitance is dependent on the instantaneous thickness of absorbent core 9 of the diaper and of air gap 14 (FIG. 3). Resistance 34 is the equivalent resistance of infant body 12. Capacitance 36 is the fixed capacitance between coupling pads 23A and 24A, while capacitance 37 is the fixed capacitance between coupling pads 23B and 24B. Equivalent circuit 35 comprises detector 20A, fixed capacitance 36, variable capacitance 31, resistance 34, variable capacitance 32, and fixed capacitance 37, which are all connected in series.

As well known, the combined capacitance of capacitors in series is the reciprocal of the sum of the reciprocal of the capacitances. In order to be able to accurately detect and transmit the instantaneous capacitance between a capacitor plate and the infant body, which is indicative of whether the infant has normal breathing patterns, the value of the fixed capacitance therefore is preferably, but not necessarily, greater than the value of the variable capacitance, which is serially connected therewith. The equivalent capacitance of circuit 37 is therefore dominated by variable capacitances 31 and 32, while resistance 34 does not considerably affect the capacitance measurement. Detector unit 20A is adapted to sense the total equivalent capacitance of circuit 37, and by comparing the total equivalent capacitance over time, i.e. with respect to several breaths or with respect to previous measurements, it is able to determine whether the infant has normal breathing patterns. By comparing the total equivalent capacitance with a nominal value, which is generally empirically measured, detector 20A may also advantageously determine whether air gap 14 is of an average value, much smaller than the nominal value indicating that the diaper is loosely attached to the infant, or much greater than the nominal value indicating the diaper is attached to the infant in an excessively tight manner, whereupon a parent is alerted.

In order to allow for manufacturing tolerances and mechanical movement of the detector within the pocket, it is desirable that diaper side coupling pads 23A-B be of a larger size than the corresponding detector side coupling pads 24A-B, so that the entire area of a diaper side coupling pad overlap the corresponding detector side coupling pad, so that the coupling capacitance between a diaper side coupling pad and the corresponding detector side coupling pad remains constantly high.

Figure 5:
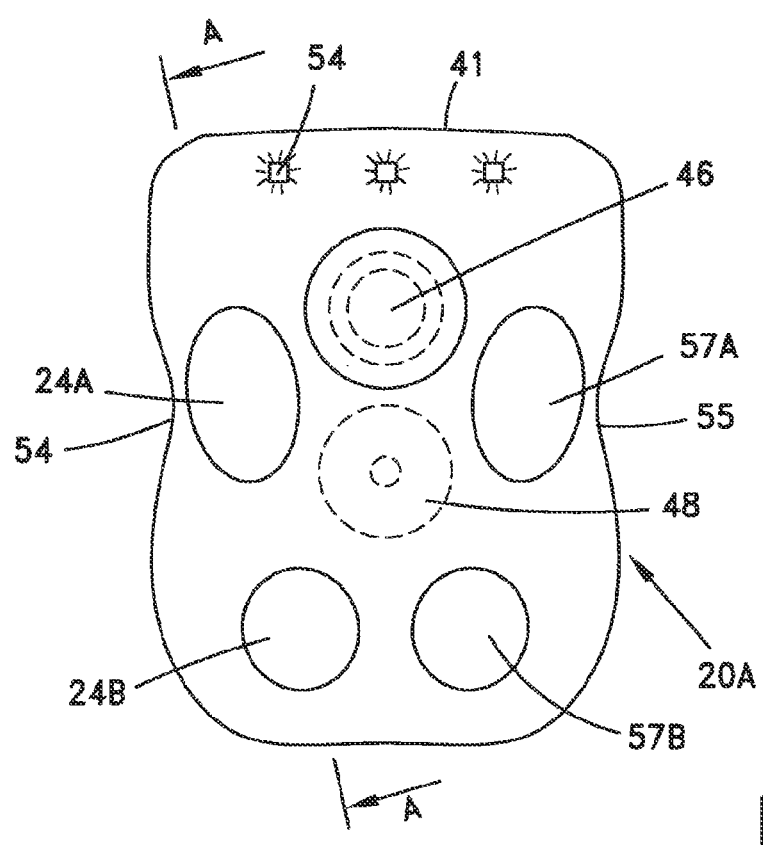
FIGS. 5 and 6 illustrate a top view and a cross-sectional view from the side, respectively, of a detector unit.
Figure 6:
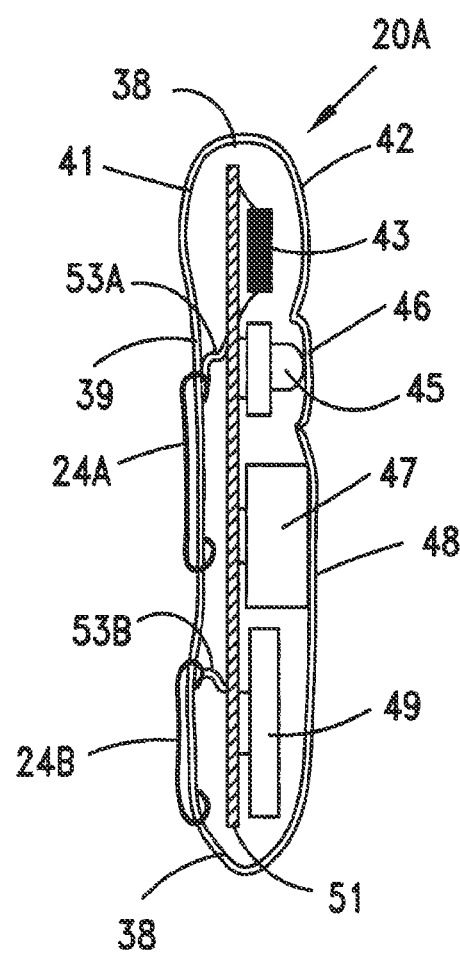

FIGS. 5 and 6 illustrate a top view and a cross-sectional view from the side, respectively, of a detector unit 20A. The components of detector 20A are mounted within casing 41, which may be made of plastic material, while being sealed and water resistant. Casing 41 is ergonomically configured with a thin and curvilinear structure that is shaped without any sharp protrusions, so that when retained in pocket 8A (FIG. 3), casing 41 does not cause any discomfort to the infant when a portion of the infant body is pressed thereagainst. Arcuate side portions 38 of casing 41, which may contact pocket 8A (FIG. 3) by means of opposed side recessed portions 54 and 55 for engaging complementary protrusions of the pocket, are integrally formed with underside 39 and with upper portion 42 thereof.

Detector unit 20A comprises a microcontroller 43, a recessed button 45 for activating or deactivating microcontroller 43, for silencing an enunciated alarm signal, or for any other desired user input, upon depression of an overlying region 46 of upper casing portion 42, an enunciator 47, e.g. of the piezoelectric or electromagnetic type, for audibly alerting a parent when symptoms of apnea are detected and placed beneath a thin layer 48 of upper casing portion 42 to minimize the attenuation of the alarm signal, a battery 49, e.g. of the CR2032 coin cell type, a flexible or rigid printed circuit board 51 electrically connected to microcontroller 43, button 45, enunciator 47, and battery 49, and coupling pads 24A-B externally attached to underside 39. A portion of coupling pads 24A-B protrudes through underside 39 and is connected with conductors 53A-B, respectively, which in turn are electrically connected with printed circuit board 51. One or more light, LED, or any other suitable optical indicator, in communication with microcontroller 43 may be used to visually alert a parent if casing 41 is not opaque. Contacts 57A-B for connecting one or more additional sensors are also connected to underside 39.

Figure 7:
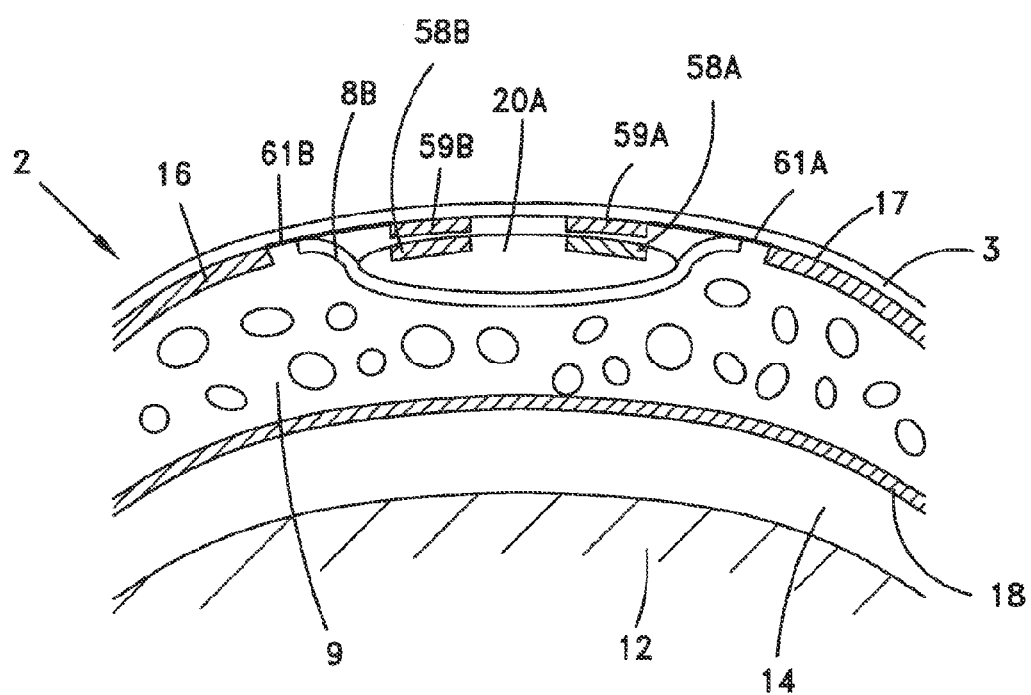
FIG. 7 is a schematic cross sectional view of a front section of a diaper provided with the detector of FIG. 2, according to another embodiment of the invention.

FIG. 7 illustrates front section 2 of a diaper, which comprises outer layer 3, absorbent core 9, and inner layer 18, showing the connection in magnified cross sectional view between plates 16 and 17 and detector unit 20A. Detector unit 20A is placed within pocket 8B, which is welded or bonded to the inner face of the waterproof outer layer 3 of the diaper. Although pocket 8B is embedded within absorbent core 9, it can be easily accessed by means of a suitable incision effected in diaper outer layer 3.

In this embodiment, detector unit 20A is directly connected to sensor plates 16 and 17. Detector side contacts 58A-B attached to the exterior face of casing underside 39 (FIG. 6) of detector 20A are electrically connected to diaper side contacts 59A-B, respectively. Contacts 59A-B in turn are electrically connected to plates 17 and 16, respectively by means of conductors 61A-B, respectively, which are attached to the inner face of outer layer 3, extending from a diaper side contact to a corresponding plate. The electrical connection between a detector side contact and a corresponding diaper side contact is sustained by minimizing the clearance between the walls of pocket 8B and the casing of detector 20A, so that the walls of pocket 8B will apply a sufficiently high outwardly directed force, i.e. towards outer layer 3, to detector unit 20A, and by providing a suitable texture and/or structure to the contacts 58A-B and 59A-B.

Figure 8A:
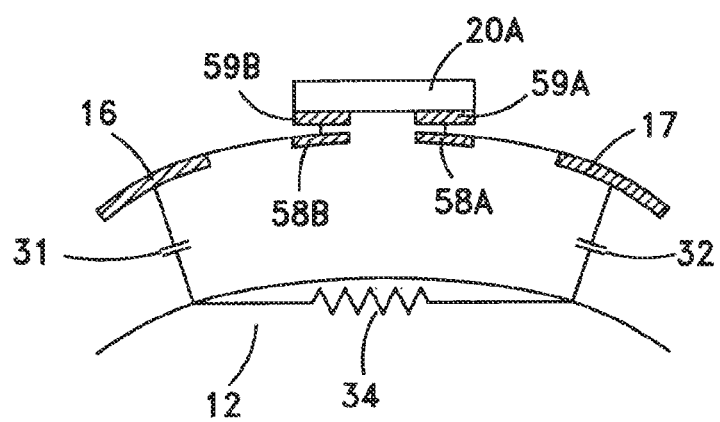
FIG. 8A is a schematic illustration showing the electrical equivalent of each component of the detector of FIG. 7, including the contribution of an infant body.
Figure 8B:
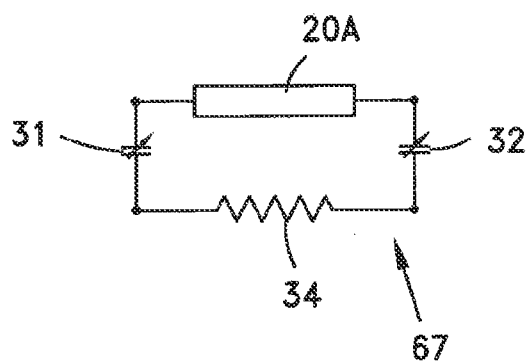
FIG. 8B is an electrical circuit corresponding to FIG. 8A.

FIGS. 8A-B schematically illustrate the electrical equivalent of the circuit 67 defined by the apparatus of this embodiment. As shown, capacitance 31 and capacitance 32 are the variable capacitances between plates 16 and 17, respectively, and infant body 12, wherein the variable capacitance is dependent on the instantaneous thickness of absorbent core 9 of the diaper and of air gap 14 (FIG. 3). Detector unit 20A is connected to capacitance 31 by means of contacts 58B and 59B, and is connected to capacitance 32 by means of contacts 58A and 59A. Thus equivalent circuit 67 comprises detector unit 20A, variable capacitance 31, resistance 34, and variable capacitance 32, which are all connected in series. The resistance of infant body 12 and contacts 58A-B and 59A-B, which are connected in series, do not significantly affect the measurement of the equivalent capacitance.

Figure 9A:
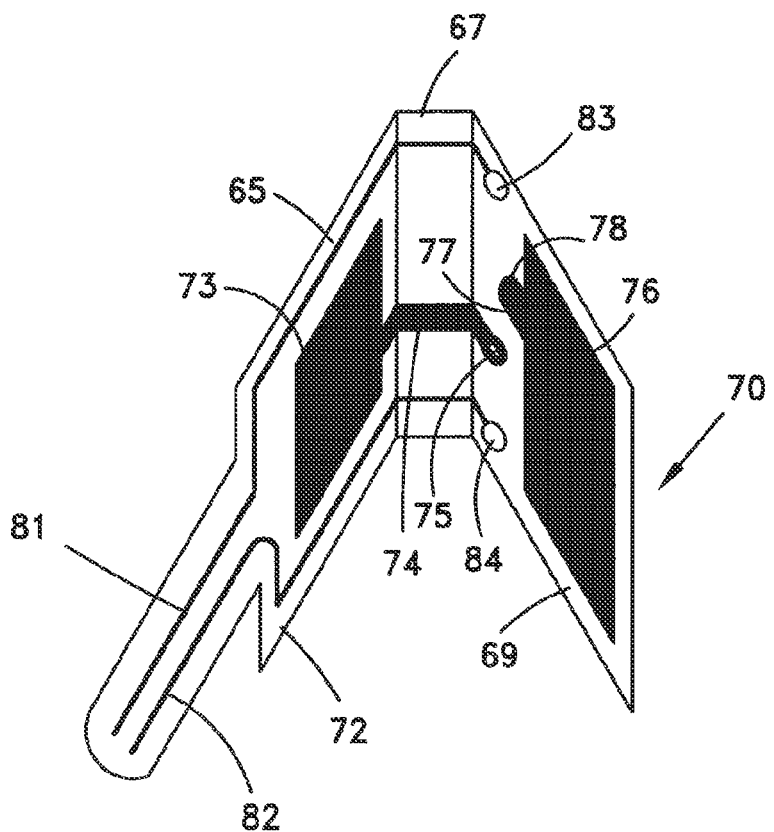
FIG. 9A is a perspective view of another embodiment of a capacitive type sensor.

FIG. 9A illustrates another embodiment of a capacitive type apnea sensor, which is designated by numeral 70. In the capacitive type sensor of FIG. 9A, the capacitance between capacitor plates is sensed, and an apnea alarm responds to variations of the sensed capacitance.

In some embodiments, sensor 70, which is shown partially folded, comprises a flexible substrate 72, e.g. made of paper, card or thin plastic, and two spaced rectangular conductive elements 73 and 76, which constitute capacitor plates, applied to the same face of substrate 72 by conductive ink, hot foil stamping, bonding, or vacuum metallization. Substrate 72 is folded to define an inner portion 65 that includes element 73, an outer portion 69 that includes element 76, and a crease 67 interposed between inner portion 65 and outer portion 69. Conductive strip 74 extends from conductive element 73 to outer portion 69 without contacting element 76, and aperture 75 is bored at the terminal end of strip 74. Curved conductive appendage 77 extends from element 76, and aperture 78 is bored therein. An electrically insulating layer may be applied to conductive elements 73 and 76, strip 74, and appendage 77.

It will be appreciated that substrate 72 may be folded in any other desired fashion, so that in such a configuration conductive elements 73 and 76 may be applied to different faces of substrate 72.

In some embodiment, it is possible to deploy the capacitor plates 73 and 76 so that mechanical force transferred from the surface of the patient during his/her breathing cycle cyclically modifies a distance between plates 73 and 76. For the present disclosure, a "transfer of mechanical force" excludes the case of hydraulic and/or pneumatic means. In this example, surface of the subject's body moves up and down during breathing, increasing and decreasing upward pressure from the body surface to one or both of the plates. This increasing and decreasing outward pressure from the surface/skin of the subject may mechanically move one or more 'capacitive plates' closer together or farther apart, cyclically modifying the capacitance between the plates according to the breathing cycle. In some embodiments, it is possible to monitor the temporal variance of the capacitance, and when the capacitance between the capacitor plates or its temporal variance indicates a symptom of apnea, to generate an alarm signal.

In one non-limiting example, at least a portion of an article clothing (for example, a diaper) is located between or "sandwiched between" the plates 73 and 76. In another example, some sort of sponge is located between or "sandwiched between" the plates 73 and 76. In yet another example, there is no 'material' between plates 73 and 76 other than air.

It is appreciated that the capacitor "plates" 73 and 76 are not required to be flat and/or rectangular as shown in the figure.

Figure 9B:
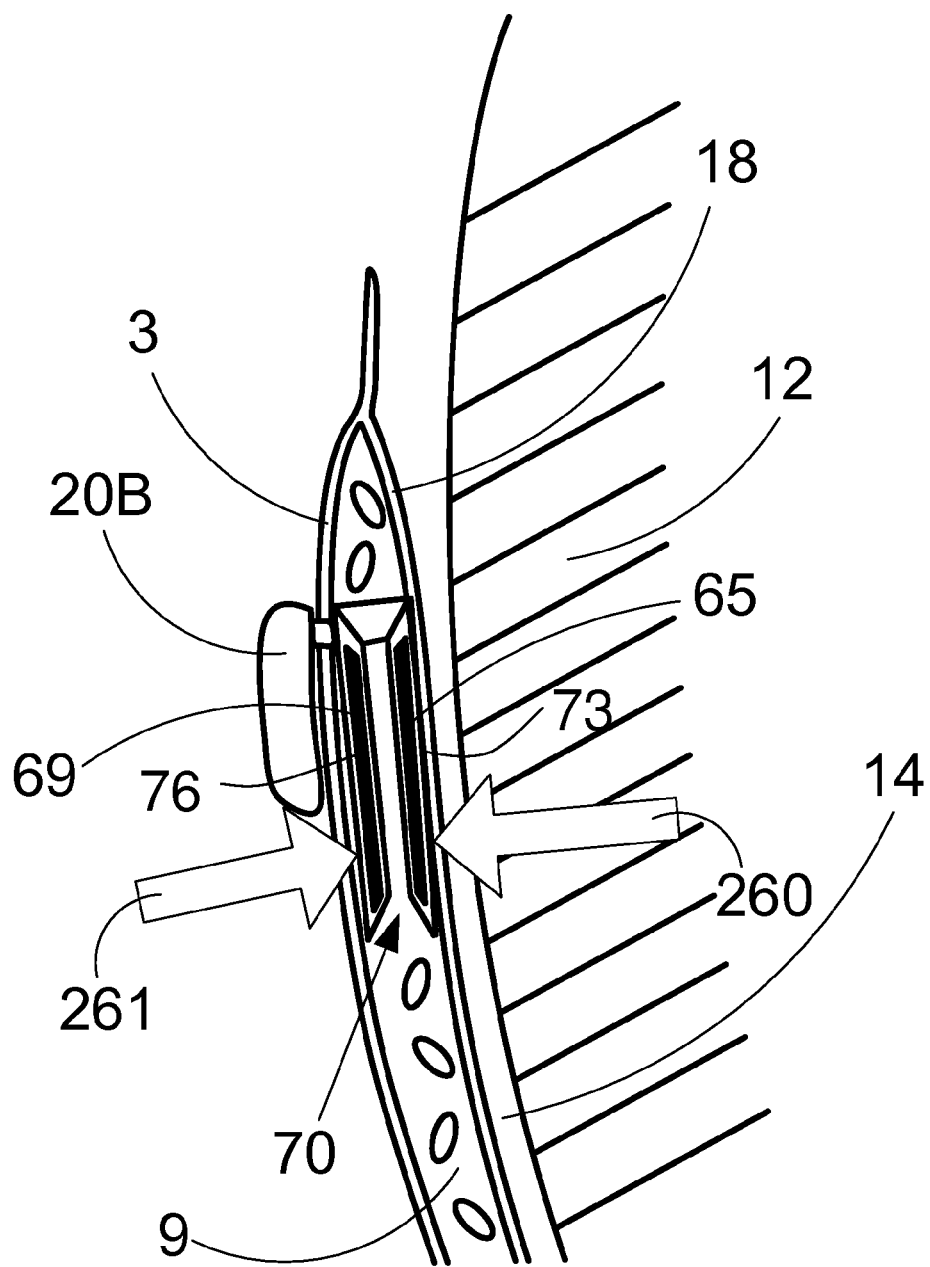
FIG. 9B illustrates a cross-section of the capacitive type sensor of FIG. 9A.

Some embodiments of the present invention relate to a method of detecting apnea that is carried out at a time when capacitive plates 73 and 76 are mechanically coupled and/or deployed to an article of clothing worn by the subject (e.g. including but not limited to a diaper). The method comprises the steps of: (a) for first 73 and second 76 capacitive plates, each capacitive plate being deployed to the article of clothing, sensing a capacitance between the first and second capacitive plates; (b) analyzing time variations of one or more of the sensor-output electrical signals to determine if the time variations are indicative of a symptom of apnea in the subject; and (c) generating an apnea alert signal that is contingent on the results of the apnea determining FIG. 9B illustrates a cross-section of the capacitive type sensor of FIG. 9A. As illustrated in FIG. 9B, the outward force from the subject's breathing 260 may cyclically increase and decrease in value (even reach a value of zero or a negative value). This force from the subject's body (e.g. the surface or skin) is transferred mechanically (i.e. see the arrow of 260) without any need for pneumatic or hydraulic force-transfer means to one or both of the capacitive plates 73, 76. In some embodiments, an additional inward force 261 in reaction to the outward force 260 may also act upon (i.e. mechanically without any need for pneumatic or hydraulic force-transfer means) one or both plates 73, 76 thereby influencing the capacitance between the plates which may be sensed and used to apnea detecting.

Figure 10:
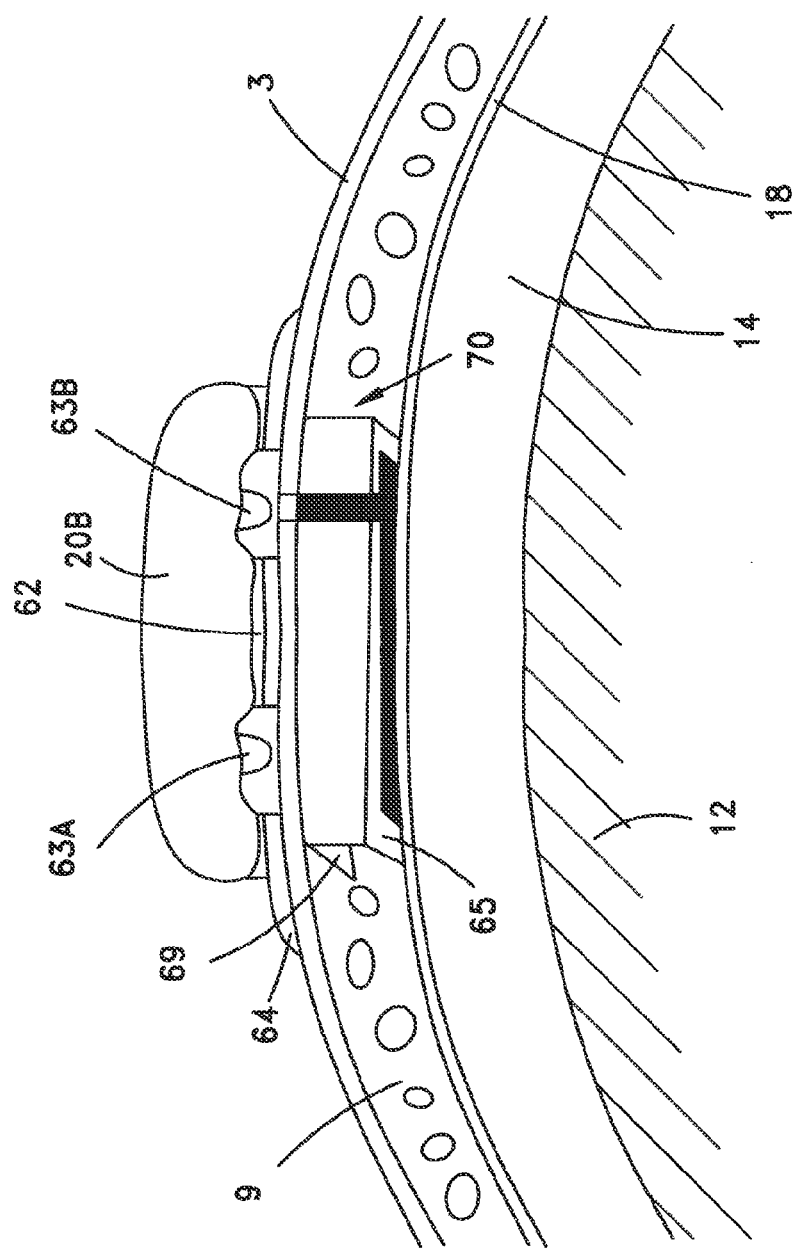
FIG. 10 is a schematic cross sectional view of a front section of a diaper provided with the sensor of FIG. 9A.

As shown in FIG. 10, sensor 70 is embedded within absorbent core 9 of a diaper in such a way that inner portion 65 and outer portion 69 face each other. Outer portion 69 of the substrate may be attached to outer layer 3 of the diaper and inner portion 65 of the substrate may be attached to inner layer 18 of the diaper. Detector unit 20B, in which are housed the same components as detector unit 20A (FIG. 6), is coupled to sensor 70 such that it is mounted externally to diaper outer layer 3. Detector unit 20B may be coupled to sensor 70 by means of metallic rivets (not shown) in engagement with apertures 75 and 78 (FIG. 9A) and in electrical communication with circuit board 51 (FIG. 6). The rivets also facilitate attachment of outer portion 69 of the substrate to outer layer 3 of the diaper. Alternatively, the underside of the casing of detector unit 20B may be provided with a backing 62 made of Velcro® (hook and loop fasteners), which is adapted to be coupled with complementary material 64 attached to the outer face of diaper outer layer 3, and with electromechanical snap connectors 63A-B, which are adapted to engage with complementary terminals, respectively, attached to outer layer 3 and in electrical communication with a corresponding conductive element. If so desired, the Velcro® material may be afforded conductive properties. It will be appreciated that a detector unit 20A provided with capacitive coupling pads, as illustrated in FIG. 6, may also be employed.

As the infant inhales and exhales, the thickness of air gap 14 diaper inner layer 14 and infant body 14 periodically changes, causing substrate inner portion 65 to be displaced and the absorbent core material to be compressed. The displacement of substrate inner portion 65 with respect to the substantially stationary substrate outer portion 69 results in a varying capacitance corresponding to that of the absorbent core material interposed between conductive elements 73 and 76, indicating that the infant has a normal breathing pattern.

With reference to FIG. 9A, an additional sensor, such as a urine and/or feces detector, in addition to apnea sensor 70, can be applied to substrate 72. The additional sensor comprises electrodes 81 and 82, which are also applied to substrate 72 and bored with apertures 83 and 84, respectively, in electrical communication with the detector. Apertures 83 and 84 may be arranged such that they are collinear with apertures 75 and 78 of the conductive elements. To enhance the sensing of bodily excretions, substrate 72 may be produced from material having superior liquid-wicking and electrical conduction properties. Electrodes 81 and 82 may be applied to substrate inner portion 65 as shown, or alternatively, to substrate outer portion 69.

FIGS. 11-14 illustrate another embodiment of the invention wherein the apnea sensor is adapted to measure periodic changes in the curvature of a body surface of an infant. Periodic changes in the curvature of the body surface are indicative that the infant has normal breathing patterns.

Figure 11:
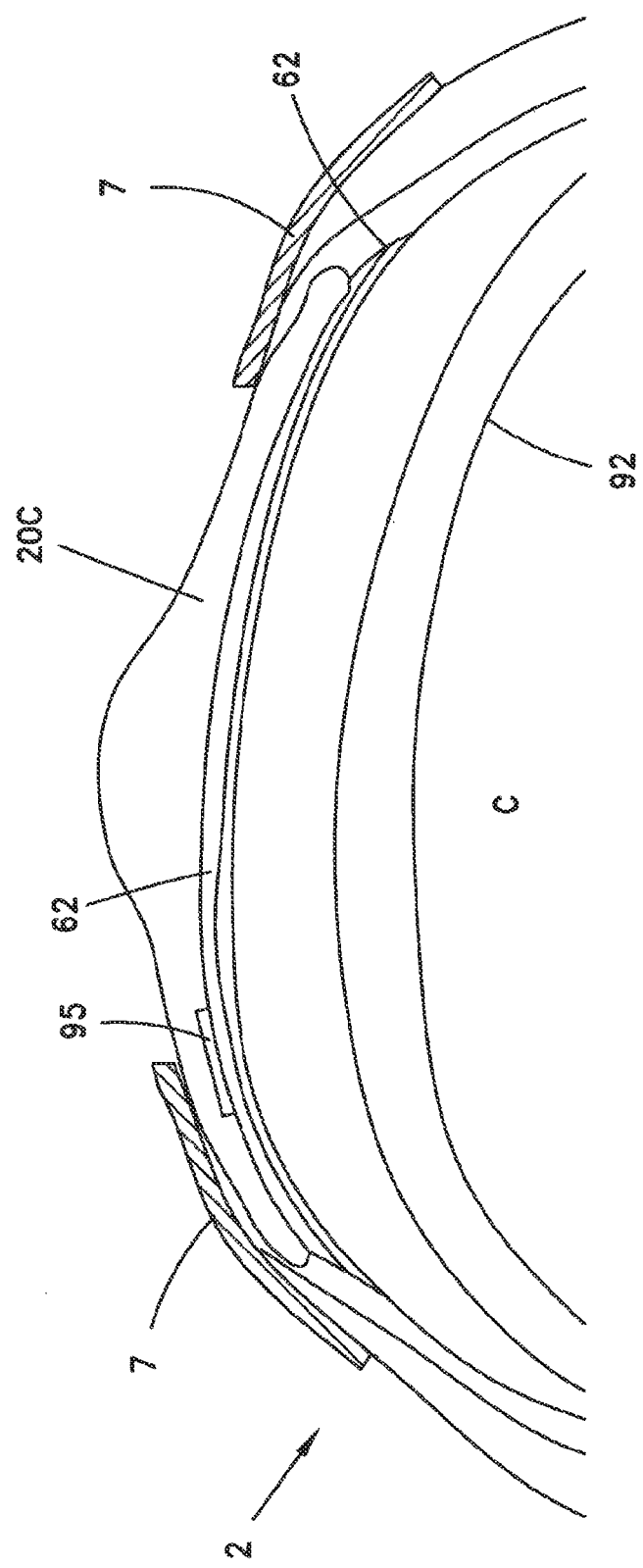
FIG. 11 is a schematic cross sectional view of a front section of a diaper provided with a curvature type sensor.
Figure 12A:
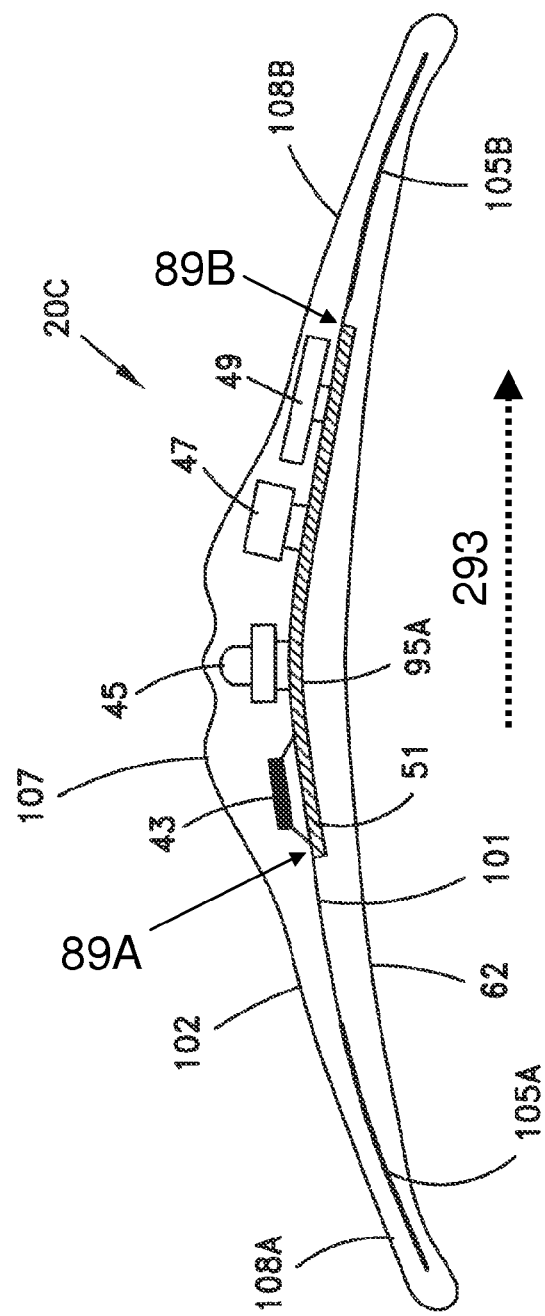
FIG. 12A is a schematic illustration of the detector unit of FIG. 11.

As shown in the example of FIG. 11, sensor 95 is adapted to measure the curvature C of body surface 92 of an infant. Sensor 95 is in communication with detector unit 20C, which is shown to be attached to front section 2 of a diaper by means of a backing 62 made of Velcro® and adhesive strips 7. Sensor 95 may include a resistive strain gauge, a flexion sensor, a piezoelectric transducer, a sensor including one or more of piezoresistive materials, a fiber optic element for measuring bending or stretching by means of optical refraction, diffraction, scattering, transmissivity, or polarization, a force-sensitive resistor, or any other sensor well known to those skilled in the art. As will be discussed below, the output of curvature sensor 95 is significantly influenced and/or governed primarily by perpendicular forces on sensor 95. FIG. 12A illustrates a schematic, cross sectional view of detector unit 20C, and FIG. 12B illustrates a perspective view from the rear of detector unit 20C.

Figure 12B:
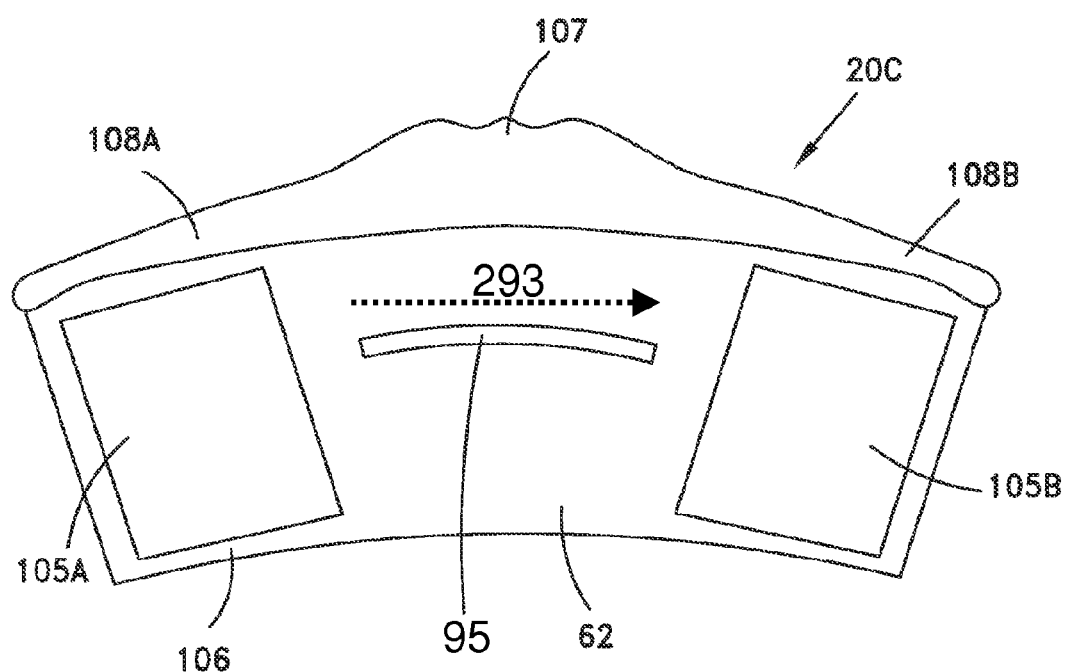
FIG. 12B is a perspective view from the rear of the detector unit of FIG. 12A.

The particular example of FIGS. 12A-12B relate to a 'hybrid detector' that include both (i) elements for detecting capacitance (e.g. 105A, 105B) (ii) as well as a curvature sensor (for example, which outputs a resistance parameter that is governed by a measured curvature). In experiments conducted by the present inventors, it has been found that the use of the multiple sensors (i.e. capacitance and curvature sensors) may produce a device that is more accurate than a device that includes only one type of sensors. Nevertheless, it is appreciated that there is no requirement for both types of sensors to be present, and some embodiments relate to the case where a curvature sensors is provided without any required capacitance sensors (or vice-versa—i.e. where the capacitance sensor is provided without any required curvature sensor).

For the example of FIGS. 12A-12B, curvilinear housing 102 of detector unit 20C is configured with a winglike bilateral symmetry, and is provided with an elevated central portion 107 and relative thin extremities 108A-B. Microcontroller 43, recessed button 45, enunciator, 47, battery 49, and flexible circuit board 101 are housed within central portion 107. The winglike configuration of housing 102 advantageously increases the engagement area of Velcro® backing 62, and furthermore, enables attachment to extremities 108A-B by adhesive strips 7, as shown in FIG. 11. The winglike configuration of housing 102 also provides flexibility in terms of sensor selection. Flexible capacitive plates 105A-B of increased area can be embedded within, or printed on an inner surface 106 of, extremities 108A-B, respectively, for enhanced sensitivity. In the particular example of FIG. 12A, a curvature sensor such as a resistive strain gauge 95A may be deployed within central portion 107, such as printed on flexible circuit board 101 as shown. Alternatively, resistive strain gauges may be housed within extremities 108A-B, respectively. Velcro® backing 62 may be applied to the entire inner surface 106, or a portion thereof.

It is appreciated that strain gauges may measure a force or stress caused by 'pulling' on the ends of strain gauge 95A (i.e. parallel tensile stress)—therefore, the strain gauge 95A is not, by itself a curvature sensor 95 which measures 'perpendicular forces' that are perpendicular to a tangent 293 around the circumference of the patient and/or perpendicular to a "flat surface" the substantially flat curvature sensor 95. Therefore, in the example of FIG. 12A, one or more mechanical elements may be provided to 'translate' radially-outward force that is substantially perpendicular to a length of the strain gauge and/or perpendicular to a vector connecting stretchable ends 89A, 89B into a tension and/or compression that is substantially parallel to tangent 293.

In one example, strain gauge is embedded within central portion 107 which is semi-rigid or substantially rigid (but not completely rigid). In this example, because strain gauge 95A is embedded within the semi-rigid or substantially rigid material, radially outward force caused by the subject's breathing that is perpendicular to 293 and/or perpendicular to the substantially flat surface of strain gauge 95A is 'diverted around' or 'transferred to' ends 89A and 89B. Thus, the semi-rigid or substantially rigid material converted a force perpendicular to the substantially flat surface to one which 'pulls the ends' of this substantially flat surface and can then be measured by strain gauge 95A—thus, strictly speaking, strain gauge 95A is not by itself a curvature sensor 95 but rather is a part of a curvature sensor 95.

In yet another example, an end 89A of strain gauge is attached to "flexible" printed circuit board 101 (which is not that 'flexible' and which, in reality, is known to be at least semi-rigid), and flexible printed circuit board 101 plays a roll in converting the outward force perpendicular to tangential axis 293 into force along tangential axis 293—for example, according to a mechanism similar to the mechanism explained below with reference to FIG. 14E.

In order to support connectivity to other disposable sensors such as urine detection electrodes, selected regions of Velcro® backing 62 may have electrically conductive properties.

Alternatively, adhesive strips 7 (FIG. 11) may be conductive, so as to connect a sensor to external contacts provided on housing 102.

Figure 13A:
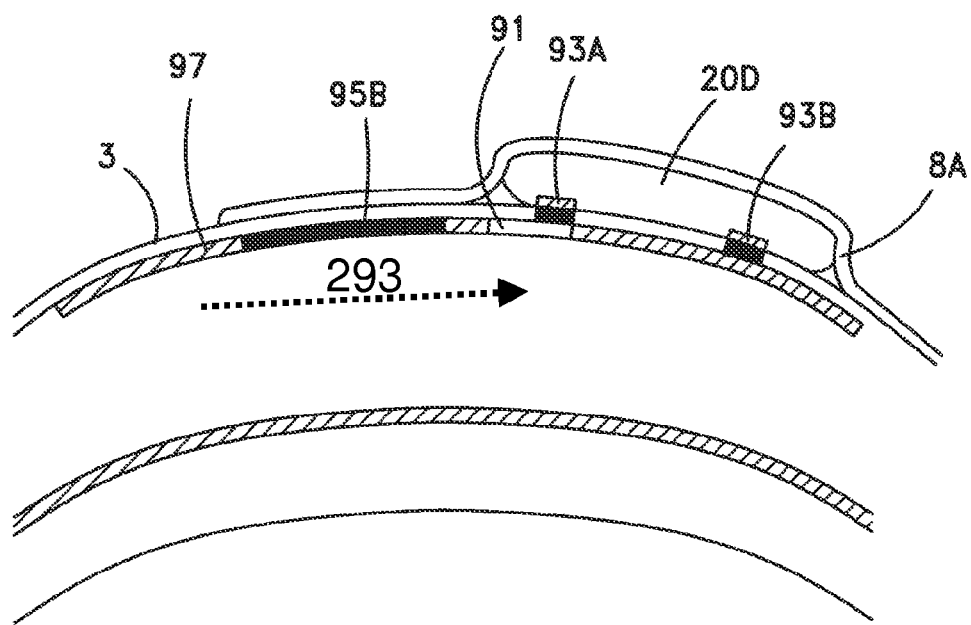
FIG. 13A is a magnified view of the connection between a curvature type sensor and a detector unit, according to one embodiment of the invention.

In FIG. 13A, the curvature sensor is shown to be a flexion sensor 95B, such as one manufactured by Flexpoint Sensor Systems, Inc., Draper, Utah, USA, which is adapted to convert the bending of a substrate into a variable resistance. Detector unit 20D is retained within pocket 8A attached to the outer face of diaper outer layer 3, and is in communication with flexion sensor 95B by means of conductor 91 connected to flexion sensor 95B and contacts 93A-B of detector unit 20D, which are in communication with conductor 91. By mounting, or directly printing, flexion sensor 95B on a semi-flexible insert 97 attached to the inner face of diaper outer layer 3, any change in the curvature of the diaper, such as a result of breathing movement, can be sensed as a periodic change in resistance.

Figure 13B:
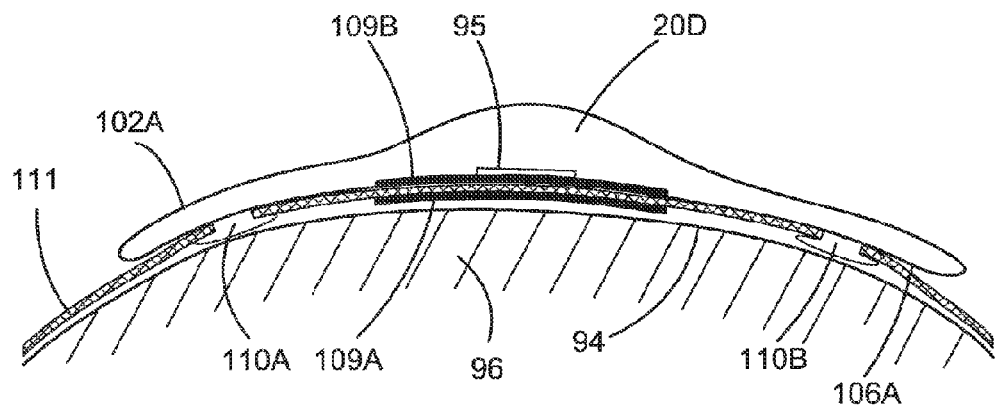
FIG. 13B is a schematic cross sectional view of a detector unit that is releasably attached to an article of clothing and provided with a curvature type sensor.

FIG. 13B illustrates a detector unit 20D for determining when an adult subject is suffering from apnea. Detector unit 20D comprises curvature sensor 95, e.g. sensor 95A of FIG. 12A or sensor 95B of FIG. 13A, and is adapted to measure the curvature of body surface 94 of an adult 96. Housing 102A of detector unit 20D may be configured with a winglike bilateral symmetry as shown, or with any other suitable configuration. Housing 102A may be releasably attached to an article of clothing 111, such as an upper portion of pants, pajamas or underwear, or a lower portion of a shirt, by means of clips 110A and 110B attached to inner surface 106A of housing 102A. Alternatively, housing 102A may be releasably attached to article of clothing 111 by means of flexible magnets 109A-B, e.g. polymer magnets, of opposite polarity. Magnet 109A is placed between clothing article 111 and body surface 94, and magnet 109B is attached to, or integral with, inner surface 106A, so that magnets 109A and 109B will be coupled together while clothing article 111 is positioned therebetween to ensure that body surface 94 will be spaced less than a predetermined maximum distance from housing inner surface 106A.

Figure 13C:
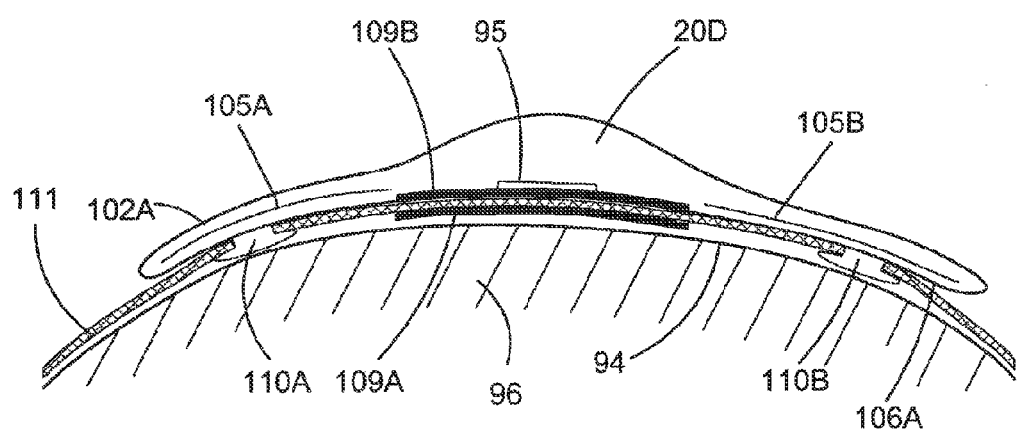
FIG. 13C is a schematic cross sectional view of a detector unit that is releasably attached to an article of clothing and provided with both a curvature type sensor and a capacitive type sensor.

In FIG. 13C, adult apnea detector unit 20E configured with housing 102A comprises both curvature sensor 95 and flexible capacitive plates 105A-B. It will be appreciated that an adult apnea detector unit may be provided solely with a capacitive type sensor. Similarly, an adult apnea detector may be employed in conjunction with any of the embodiments described hereinabove.

Figure 14A:
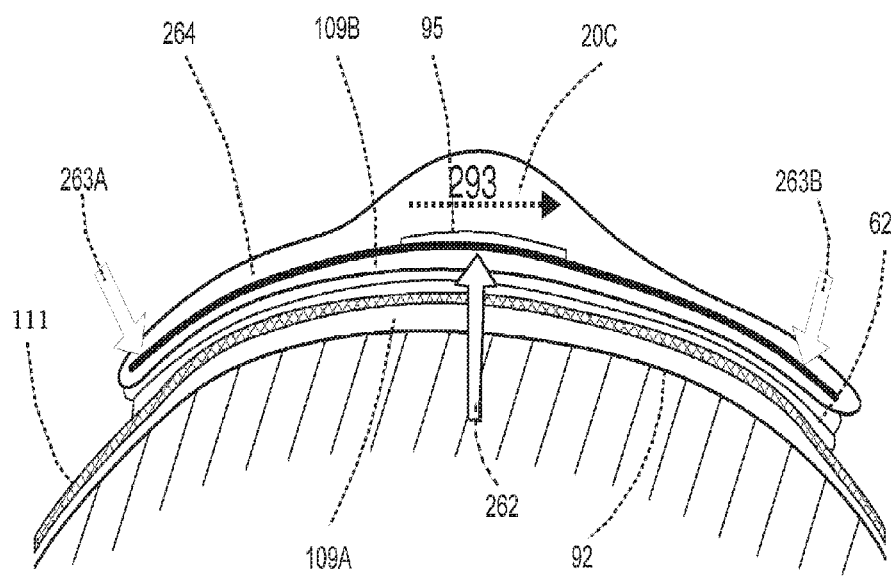
FIGS. 14A-14E illustrate some embodiments related to a curvature sensor.

In FIG. 14A, curvature sensor may be deployed together with semi-rigid or substantially rigid (but not completely rigid) substrate 264 (for example, made of semi-rigid or substantially rigid plastic). In the example of FIG. 14A, curvature sensor 95 is "above" the semi-rigid or substantially rigid (but not completely rigid) substrate 264 (or farther from the skin)—alternatively, curvature sensor 95 may be "below" the semi-rigid or substantially rigid (but not completely rigid) substrate 264.

As it shown in FIG. 14A, the length of the substrate 264 along tangential axis 14A may exceed the length of curvature sensor—for example, by a factor of at least 20% or 30% or 40% or 50% or 75% or 100% or any number. Because substrate 264 is not completely rigid, outward force 262 due to the subject's breathing will deform substrate 264 and modify the curvature of substrate 264 (for example, at least in part due to reactive forces 263A, 263B). Because substrate 264 is not flexible but is semi-rigid or substantially, forces perpendicular to a substantially flat surface of substrate 264 (i.e. even at locations within substrate 264 that are 'far' from curvature sensor 95) may cause a force perpendicular to a substantially flat surface of curvature sensor 95 to deform curvature sensor. Thus, the semi-rigid or substantially rigid substrate 264 may be said to amplify the signal of force 262.

In some embodiments, the electrical resistance parameter output by curvature sensor 95 varies as a function of time according to the breathing cycle. There is a certain magnitude in change of the electrical resistance parameter as the curvature sensor 95 senses a cyclical change in curvature. In some embodiments, (for example, related to a curvature sensor 95 that whose length (e.g. along tangential axis 293) is at most 200% or 150% or 100% or 85% or 65% or 50% of a length (e.g. along tangential axis 293) of semi-rigid or substantially rigid substrate 264), the presence of the semi-rigid or substantially rigid substrate 264 (i.e. deployed so that substrate 264 is between the subject's skin and curvature sensor 95 as shown in FIG. 14A or deployed so that curvature sensor 95 is between the subject's skin and substrate 264) significantly contributes to variations in the output electrical resistance parameter outputted by curvature sensor . Thus, in some embodiments, the absence of the semirigid or substantially rigid substrate 264 causes much smaller output resistance parameter variations output by curvature sensor 95 (i.e. output resistance parameter variations whose magnitude is at most 50%, or at most 40%, or at most 10% of a magnitude in the presence of semirigid or substantially rigid substrate 264 during the baby's breathing cycle.

Figure 14B:
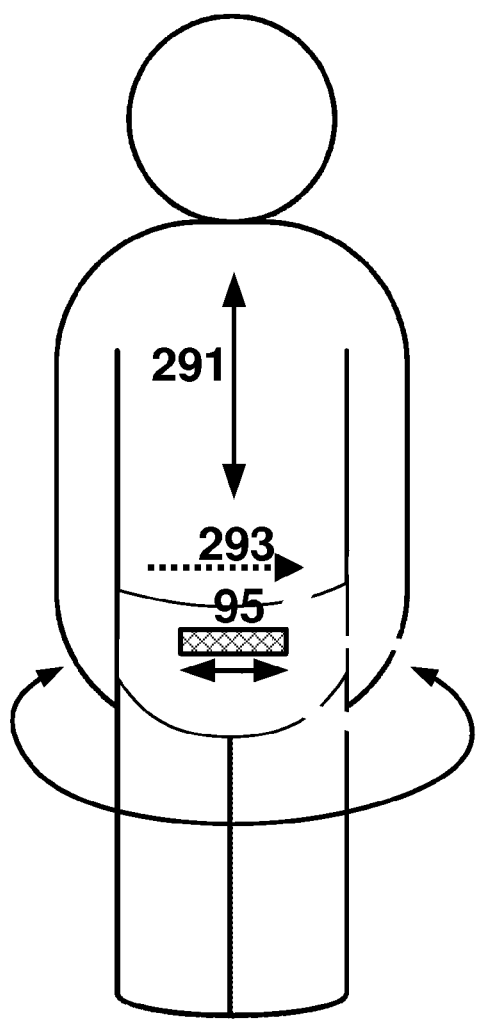

As shown in FIG. 14B, in some embodiments, sensor 95 has a 'length' of curvature sensor 95 along a circumference of the subject (i.e. along tangential axis 293) and perpendicular to an elongate axis 291 of the subject. In some embodiments, this 'length' is less than 50% or 45% or 40% or 35% or 30% of a circumference of 272 the subject at the location of curvature sensor 95. In some embodiments, the length of curvature sensor 95 (i.e. along an elongate axis and/or axis 293) is at most 25 cm.

Figure 14C:
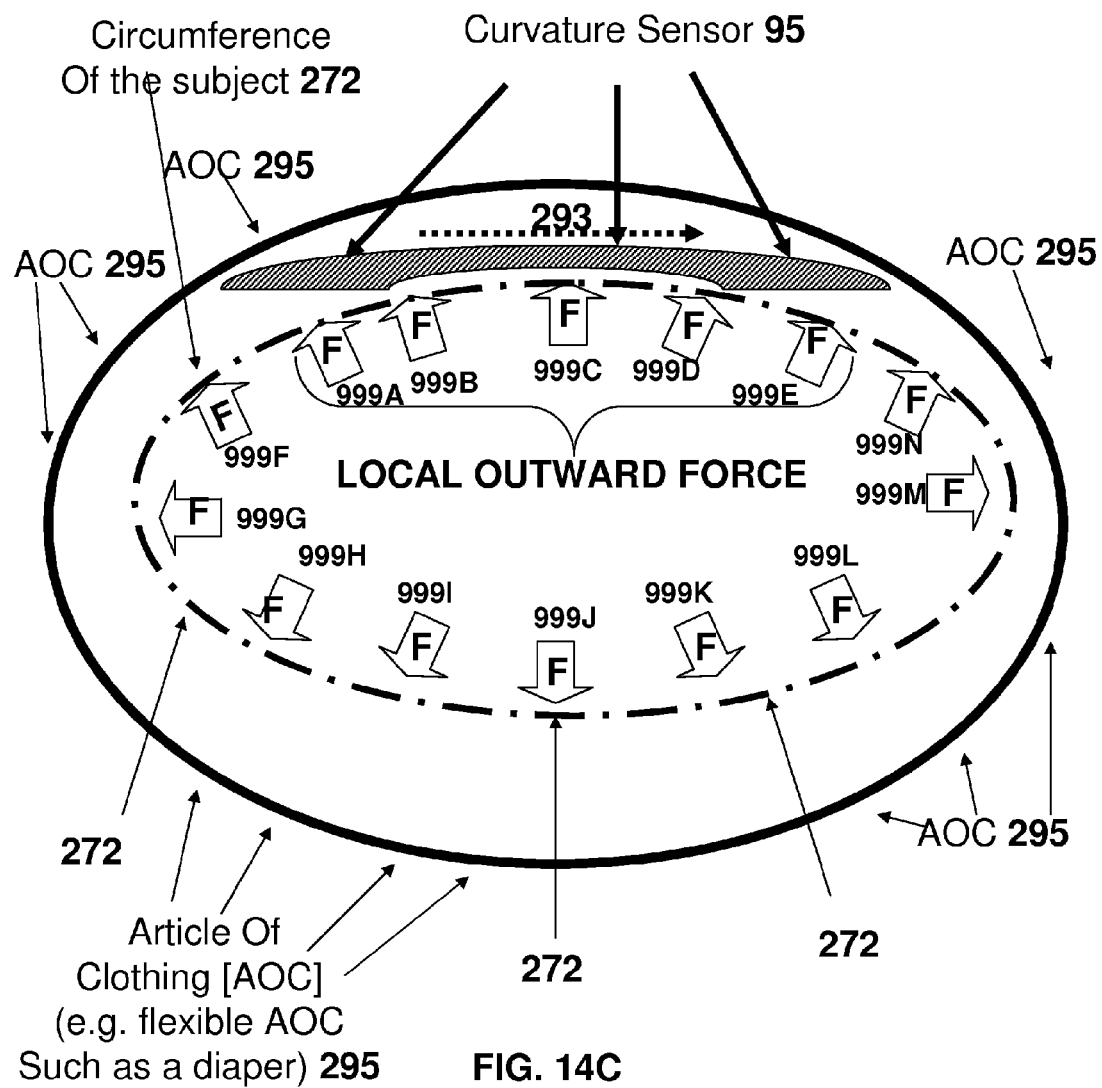
Figure 14D:
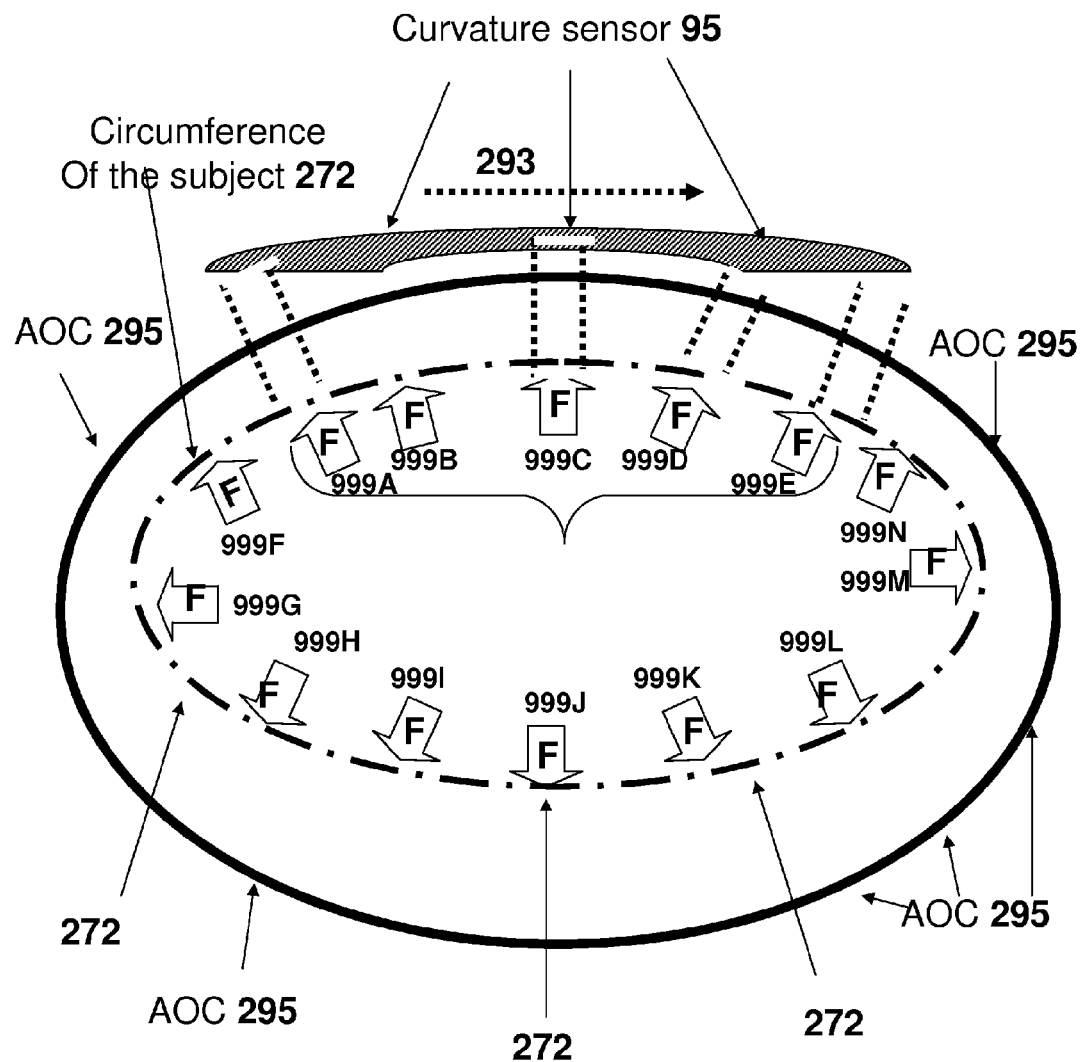

FIGS. 14C-14D relate to the definitions 'local outward force' in contrast to any 'outward force' which is caused by the breathing of the subject. The 'local outward force' relative to curvature sensor 95 is outward force at the location where the curvature sensor is deployed above the surface of the subject. Thus, in FIG. 14C (i.e. where curvature sensor 95 is deployed above the article of clothing AOC 295) and in FIG. 14D (i.e. where curvature sensor 95 is deployed below the article of clothing AOC 295) the forces identified by 999A-999E are 'local outward forces' along a vector which intersects a surface of the curvature sensor 95. In contrast, forces identified by 999F-999N are non-local. In some embodiments, the variations of the electrical resistance parameter which is output by curvature sensor during the breathing cycle are governed primarily by variations of the local outward forces during the breathing cycle—for example, which reach a maximum when the subject is inhaling and decrease when the subject is exhaling. In some embodiments, time variations in the sensed 'local outward forces' contribute at least 30% or 50% or 70% or 90% to the total variations of the output resistance parameter during the breathing cycle.

Figure 14E:
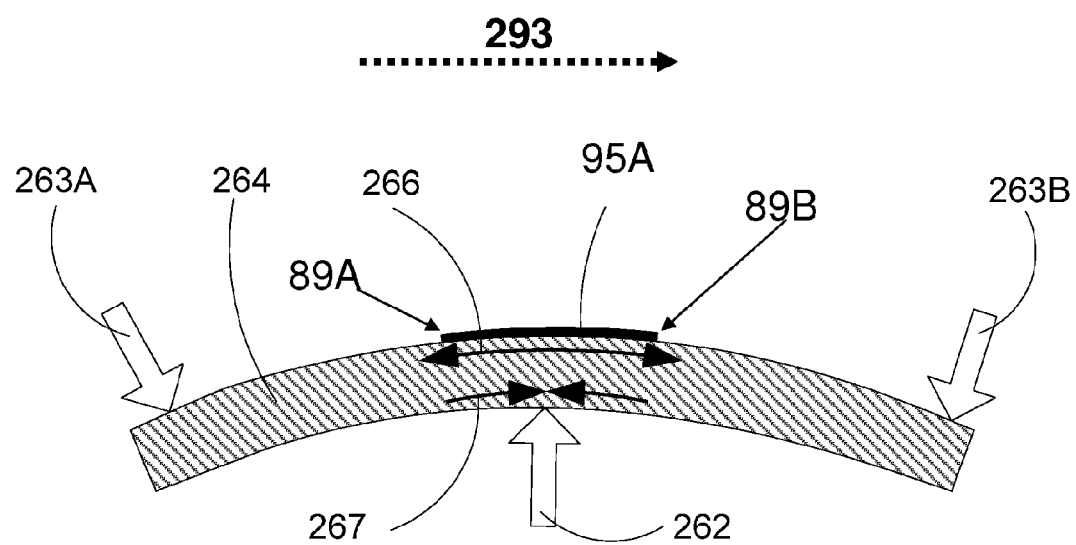

FIG. 14E relates to yet another example where curvature sensor 95 may include a strain gauge 95A. Thus, in FIG. 14E, element 264 is a semi-flexible or substantially flexible substrate 264, force 262 is an outward force from the subject due to breathing, forces 263A and 263B are reactionary inward forces from the semi-flexible substrate in reaction to force 262. The inward forces 263A, 263B cause the substrate 264 to bend and modify its radius of curvature, inducing tension 266 or compression 267 in a direction substantially parallel to axis 293. This tension or compression may be measured by strain gauge 95A which is a part of curvature sensor 95. Without the presence of a semi-flexible or substantially flexible substrate 264 as described above, strain gauge 95A by itself is not a curvature sensor 95.

In some embodiments, when curvature sensor 95 is subjected to a change in curvature from flat radius of curvature of 20 cm, the resistance parameter output by curvature sensor 95 changes by larger a percentage than when subjected to a change in tensile or longitudinal stress (e.g. along axis 293 or along an axis substantially parallel to a substantially flat surface of curvature sensor 95) from relaxed to a tensile force of 10N.

In some embodiments, curvature sensor 95 is not part of a 'closed mechanical loop' which closes upon itself to provide an inward force throughout a majority or a substantial majority (i.e. at least 60% or 70% or 80% or 90% or 95% of a circumference 272 of the subject) in response to an outward force of breathing. Instead, curvature sensor 95 may be part of a flexible article of clothing and therefore does not hinder breathing.

Figure 15:
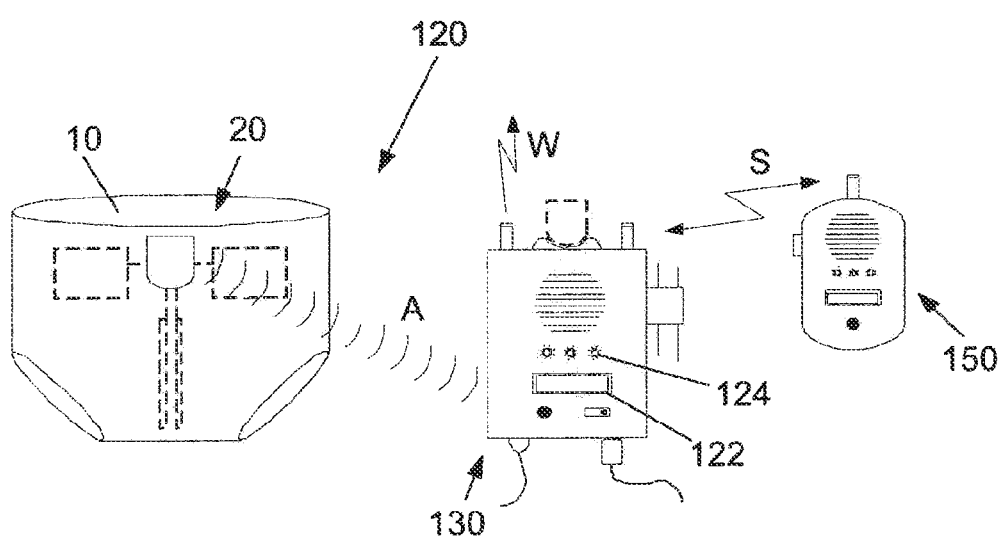
FIG. 15 is a schematic illustration of an infant monitoring system, according to one embodiment of the invention.

FIG. 15 illustrates a monitoring system generally designated by numeral 120, according to one embodiment of the present invention. System 120 comprises detector unit 20, stationary unit 130 in communication with detector unit 20, and portable unit 150 accessible to a parent or to any other authorized attendant and in communication with stationary unit 130. Detector unit 20 is embedded in diaper 10, or otherwise attached to an article of clothing, preferably in communication with an apnea sensor, as described hereinabove, and optionally with one or more additional sensors adapted to detect infant related parameters of interest, and may be configured as detector unit 20A (FIG. 6), 20B (FIG. 10), 20C (FIGS. 11-12), 20D (FIG. 13), or any other desired configuration.

As opposed to prior art detector units that are embedded or otherwise attached to a diaper and that remotely transmit sensed data by means of radio frequency (RF) waves, thereby exposing the infant to harmful levels of RF radiation, detector unit 20 advantageously transmits acoustical information to stationary unit 130. Detector unit 20 emits acoustical information A after determining that a subject related parameter of interest has a predetermined status, as sensed by one of the sensors in communication therewith. Stationary unit 130, which is supported by a selected structure, such as a bed post or a table, and is disposed within an audible range of detector unit 20, receives emitted acoustical information A and determines that it is indicative of a predetermined subject parameter status. A wireless signal S indicative of the determined subject parameter status is then transmitted to portable unit 150 via any suitable data network, so that the attendant will take corrective actions. A subject parameter status may be that a diaper is overly wet or overly tight, or that the detector unit battery is drained. When the determined subject parameter status requires immediate attention, such as when symptoms of apnea are detected, stationary unit 130 enunciates a warning signal W significantly louder than acoustical information A and displays textual information on display 122 and/or LEDs 124 become illuminated, and the authorized attendant is immediately alerted by means of portable unit 150. If so desired, detector unit 20 may be any dedicated unit for detecting a subject related parameter of interest that can transmit acoustical information to stationary unit 130, and optionally, stationary unit 130 need not be in communication with a portable unit.

When the subject is an adult who does not require an attendant, a portable unit may be unnecessary, The enunciation of acoustical information A by detector unit 20 or of warning signal W by stationary unit 130 will advantageously stimulate the subject to awake during manifestation of sleep apnea.

Figure 16A:
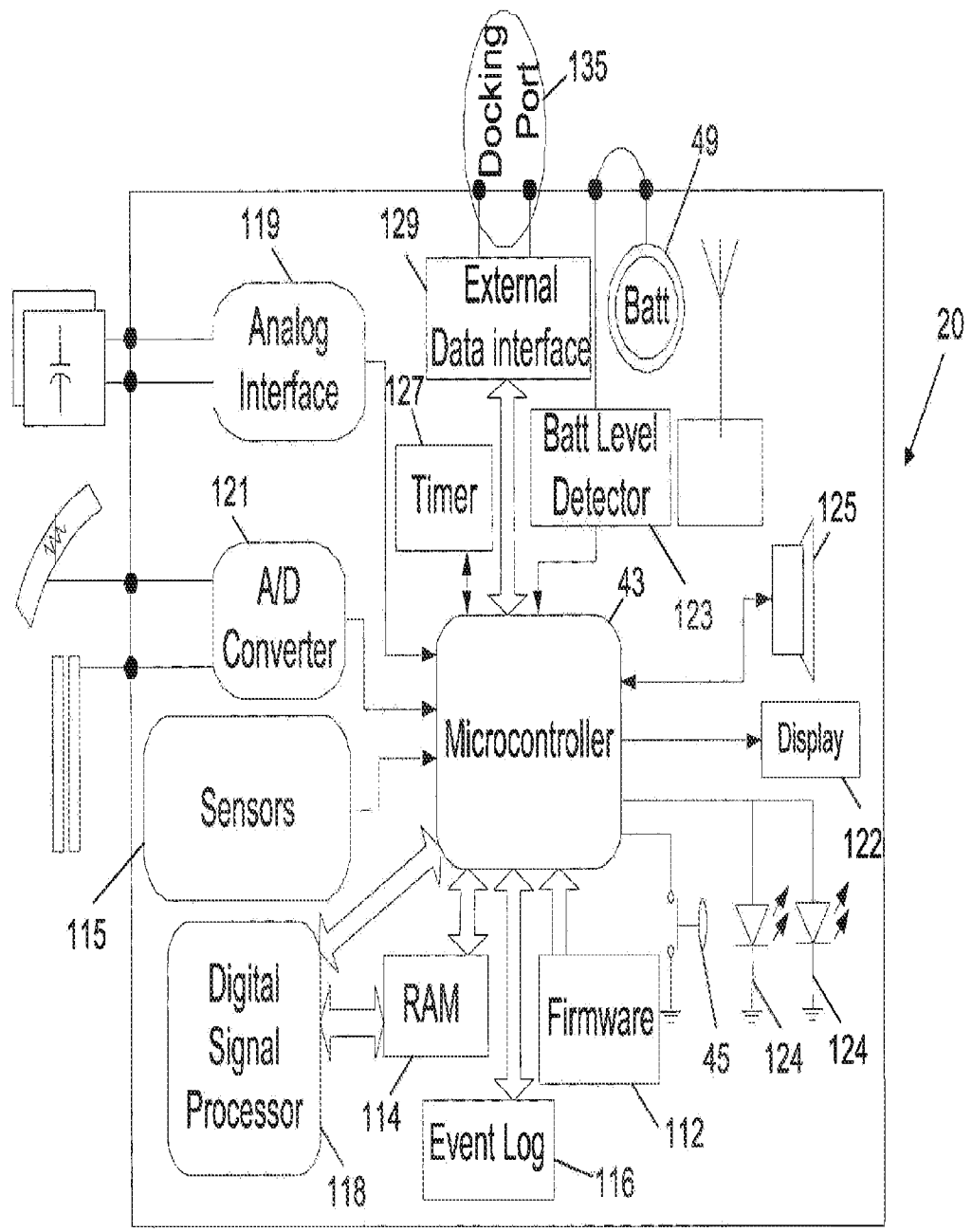
FIG. 16A is a block diagram of a detector unit, according to one embodiment of the invention.

FIG. 16A illustrates a block diagram of detector unit 20. Detector unit 20 comprises microcontroller 43, e.g. the PIC-16xxx family of microcontrollers, which is provided with memory device 112, such as Read-Only Memory (ROM) or Non-Volatile Random Access Memory (NVRAM), for storing therein firmware algorithms such as an algorithm for the detection of apnea, as will be described hereinafter, Random Access Memory (RAM) 114 including registers, event log 116, such as based on NVRAM, and digital signal processor 118. Microcontroller 43 receives input from sensors 115, including apnea sensors and additional sensors, such as urine sensor, feces sensor, ambient temperature sensor, humidity sensor, illumination level sensor, body temperature sensor, body activity sensor, oximeter, and infant sleeping orientation sensor, from analog interface 119, Analog to Digital (A/D) converter 121, and from battery level detector 123 connected to battery 49. Microcontroller 43 is also in communication with deactivation button 45, display 122, LEDs 124, enunciator 125, timer 127, e.g. an interrupt timer, and external data interface 129. Detector unit 20 is adapted to couple with docking port 135, which may be integrally attached to the stationary unit or may be an independent docking unit, to facilitate the retrieval of data stored in event log 116 by means of data interface 129, to charge battery 49, or to upgrade firmware 112.

Figure 16B:
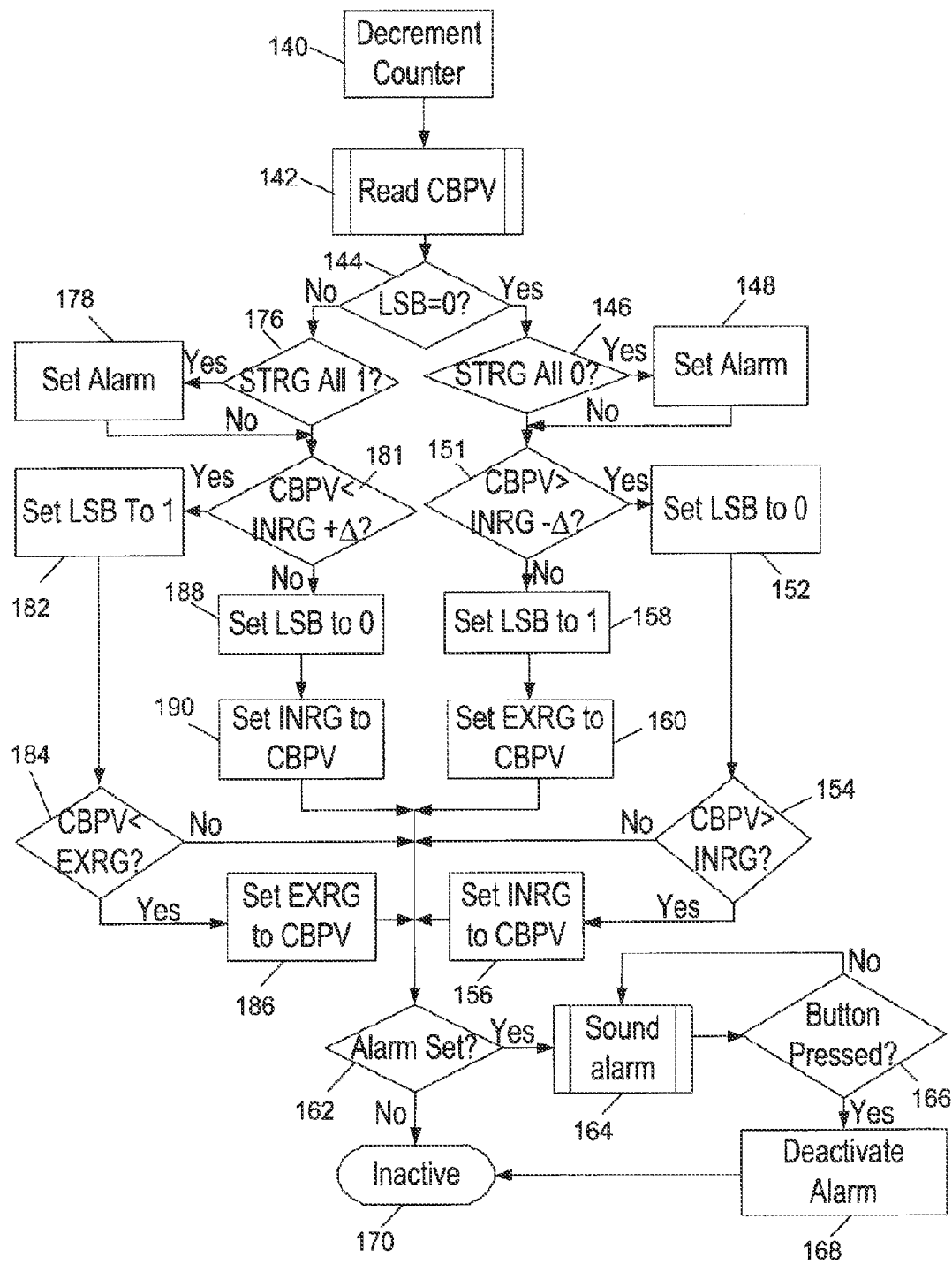
FIG. 16B is a flow diagram of steps performed by a detector unit microcontroller to detect apnea.

FIG. 16B illustrates an exemplary method for detecting apnea. The microcontroller of the detector unit receives signals from the corresponding apnea sensor, whether a capacitive type sensor or a curvature sensor as described hereinabove. The received signals are representative of a value of a parameter that is characteristic of the breathing patterns of a subject. The microcontroller processes the received characteristic breathing pattern values (CBPVs) by means of the firmware algorithm stored in the memory device and determines whether the CBPVs are indicative of the onset of apnea.

To minimize the consumption of battery power, the microcontroller operates at a low periodic sampling rate of e.g. 1 sample per 250 msec when receiving CBPVs, and is in a low-power inactive mode during the interval between two sampling operations. Even though the microcontroller is in the inactive mode, the LEDs of the detector unit are generally periodically lit to indicate that the detector unit is in operation. It will be appreciated, however, that the microcontroller can also be continuously operated, if so desired. The microcontroller is initialized during initial powerup, and is able to differentiate setup operations between the initial powerup time and a periodic powerup time. A register may be used as a counter, and the counter is decremented in step 140 after each subsequent time interval, e.g. 1 msec, has elapsed. At the predetermined periodic powerup time, a CBPV is received in step 142. In addition to CBPVs, other characteristic parameter values for the performance of auxiliary operations such as urine detection and battery level detection are received by the microcontroller at predetermined slower sampling rates, in order reduce battery consumption.

The RAM of the microcontroller has three registers: (1) a shift register in which is stored a plurality of data bits representative of a previously stored CBPV ("status register" or STRG), (2) a register in which is stored data bits representative of a maximum CBPV received during inhalation ("inhalation register" or INRG), and (3) a register in which is stored data bits representative of a minimum CBPV received during exhalation ("exhalation register" or EXRG).

The status register serves as a means for comparing the breathing patterns of the subject without need of calibration, to determine whether the onset of apnea has been detected. The least significant bit (LSB) of the shift register is set to a value of 0 after determining that the presently received CBPV is greater than the previously received CBPV, indicating that the subject is inhaling. Conversely, the LSB of the shift register is set to a value of 1 after determining that the presently received CBPV is less than the previously received CBPV, indicating that the subject is exhaling. When a LSB is stored, all of the previously stored data bits are shifted to the left and the previously stored most significant bit (MSB) is deleted. By retaining all previously stored data bits during a predetermined period of time, e.g. 10 seconds, a comparison can be made with the data bits stored in the status register to determine whether the subject is exhibiting a regular breathing pattern. That is, a regular breathing pattern is exhibited when the subject periodically inhales and exhales. However, if all the stored data bits in the status register are identical, an abnormal breathing pattern is being exhibited and a corrective action is needed.

Accordingly, the microcontroller determines in step 144 whether the LSB of the status register is set to 0. If so, the microcontroller determines in step 146 whether all data bits stored in the status register are 0. If all data bits stored in the status register are 0, the subject has been found not to be exhaling during the period equal to the product of number of bits and the interval between two sampling operations, whereupon an alarm flag is set in step 148.

If some of the data bits stored in the status register are 1, indicating that a regular breathing pattern is being exhibited, the presently received CBPV is compared with the maximum CBPV stored in the inhalation register in step 151. If the presently received CBPV is greater than the difference between the maximum CBPV stored in the inhalation register and a characteristic delta value, which takes into account hysteresis during data acquisition, such as a result of movement of the infant or partial inhalation, the LSB of the status register is set to 0 in step 152, the other bits thereof are shifted to the left and the MSB thereof is deleted. If the presently received CBPV is greater than the maximum CBPV stored in the inhalation register as determined in step 154, the inhalation register is set to CBPV in step 156. However, if the presently received CBPV is less than the difference between the maximum CBPV stored in the inhalation register and the characteristic delta value, a change in the breathing pattern is being exhibited and the LSB of the status register is set to 1 in step 158, whereupon the exhalation register is set to CBPV in step 160.

After determining whether the inhalation register needs to be set with the CBPV in step 154 or performing steps 156 or 160, a determination is then made in step 162 whether the alarm flag has been set. If the alarm flag has been set, a warning sound, which is preferably an acoustical signature defined by a predetermined number of tones each of which having a predetermined duration and frequency, is enunciated in step 164. If the deactivation button is depressed in step 166, the warning sound will not be enunciated in step 168.

This method is similarly performed for exhalation in steps 176, 178, 181, 182, 184, 186, 188, 190 when the LSB of the status register is set to 1 in step 144. The microcontroller then returns to the inactive mode in step 170 for another interval prior to another sampling operation.

Figure 17:
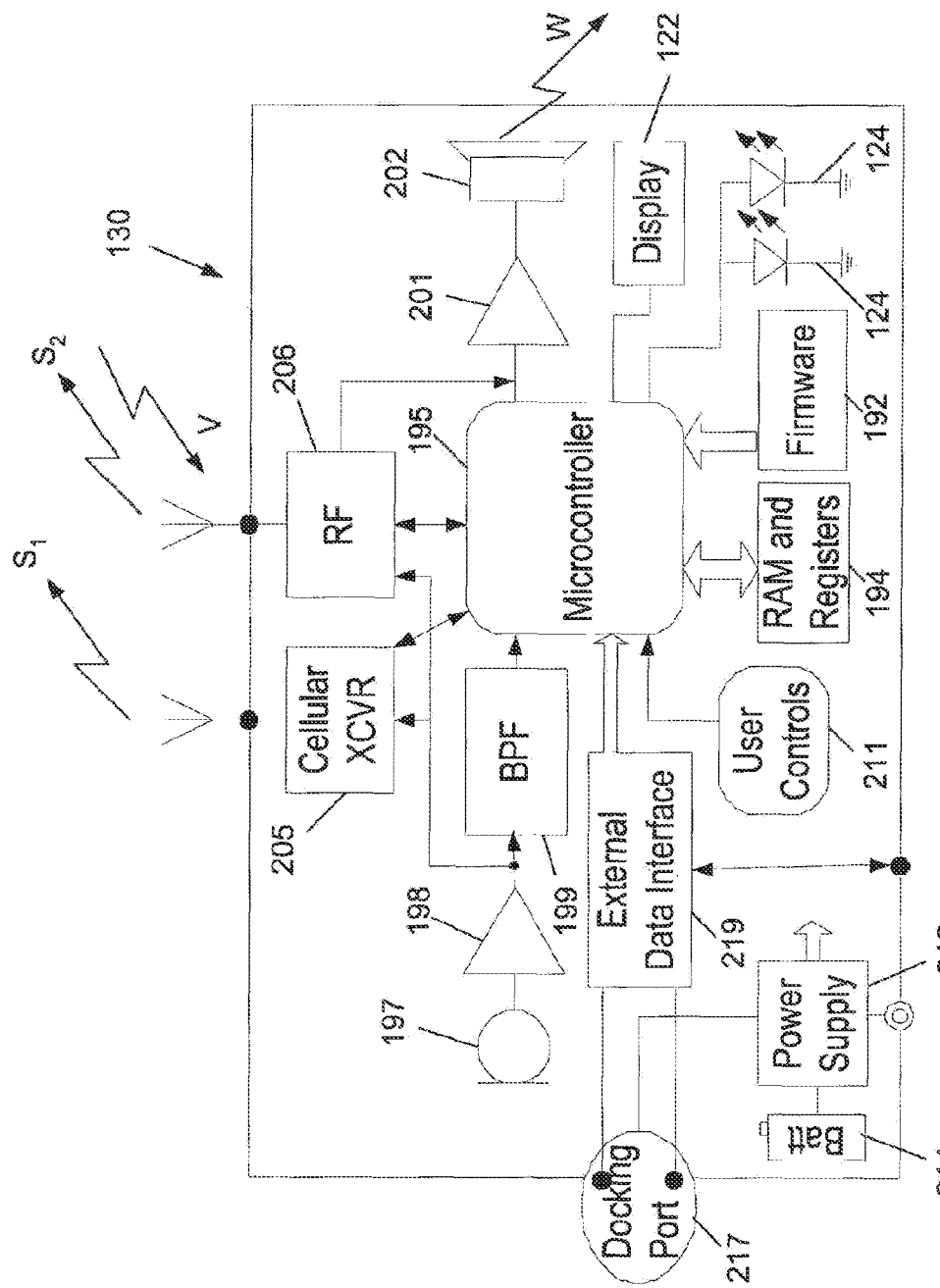
FIG. 17 is a block diagram of a stationary unit, according to one embodiment of the invention.

FIG. 17 illustrates a block diagram of stationary unit 130. Stationary unit 130 comprises microcontroller 195, which is provided with memory device 192, such as Read-Only Memory (ROM) or Non-Volatile Random Access Memory (NVRAM), and Random Access Memory (RAM) 194 including registers, microphone 197 for detecting an audio signal, e.g. an acoustical signature, emitted by enunciator 125 of detector unit 20 (FIG. 16A), amplifier 198, and audio bandpass filter (BPF) 199. BPF 199 receives an amplified audio signal and filters unwanted noise and tones that have a frequency outside the predetermined frequency band of the detector unit enunciator. The filtered signals are transmitted as digital inputs to microcontroller 195. When microcontroller 195 determines that the filtered signals are indicative of a predetermined audio signal emitted by the detector unit, a high-volume warning signal W is generated by means of amplifier 201 and speaker 202, to audibly alert an authorized attendant that a corrective action needs to be urgently taken. Alternatively, or in addition, microcontroller 195 may output textual information to display 204, e.g. a liquid crystal display (LCD), or to optical indicators 205, such as an LED.

Microcontroller 195 receives inputs from one or more user initiated controls 211, such as a dial, button or switch. Stationary unit 130 is powered by power supply 212 and a suitable power source, such as battery 214 or by means of alternating current (AC). Battery 214 may be rechargeable and serve as a backup during an outage or shortage of power supplied from the AC mains.

Data may be exchanged with microcontroller 195 by means of external data interface 219. Stationary unit 130 is adapted to couple with docking port 217, to facilitate the retrieval of data by means of data interface 219, to charge battery 214, or to upgrade firmware stored in memory device 192. Data interfacing circuits may interface between docking port 217 and microcontroller 195. These data interfacing circuits may also be connected to a universal serial bus (USB), a data network such as Ethernet, or to an Internet service provider such as by an asymmetric digital subscriber line (ADSL) line. Such data exchange enables the analysis of event log 116 (FIG. 16A), the upgrading of firmware 192 and/or the updating of configuration information and user settings. Docking port 217, which may be integrally attached to stationary unit 130, may be the same docking port to which the detector unit is coupled, and therefore is adapted to charge detector unit battery 49 (FIG. 6) and to update detector unit firmware 112 (FIG. 16A).

When a portable unit is employed, microcontroller 195 also comprises a transceiver 205 for transmitting a wireless signal $S_1$ over a cellular network and a transceiver 206 for transmitting an RF signal $S_2$. A signal $S_1$ or $S_2$, depending on with which network the portable unit is in communication, is transmitted to the portable unit when a corrective action needs to be taken. Alternatively, a signal $S_1$ may be transmitted over a cellular network to a predetermined number to alert the authorized adult who is not in an audible range of stationary unit 130 or to an emergency medical service, such as when the infant is exhibiting symptoms of SIDS, particularly sleep apnea. Alternatively, a signal $S_1$ or $S_2$ may be transmitted to a home automation system, for activating a device to alert an authorized attendant who may be asleep or does not respond to a high-volume warning signal W or to a cellular telephone call. The home automation system may turn on, or flash, lights, or actuate a vibrator to ensure that the authorized attendant will take emergency corrective actions.

Stationary unit 130 may also amplify acoustical information enunciated by the subject. The acoustical information which is received by microphone 197 is amplified and emitted by speaker 202, or transmitted by transceiver 205 or 206.

Figure 18:
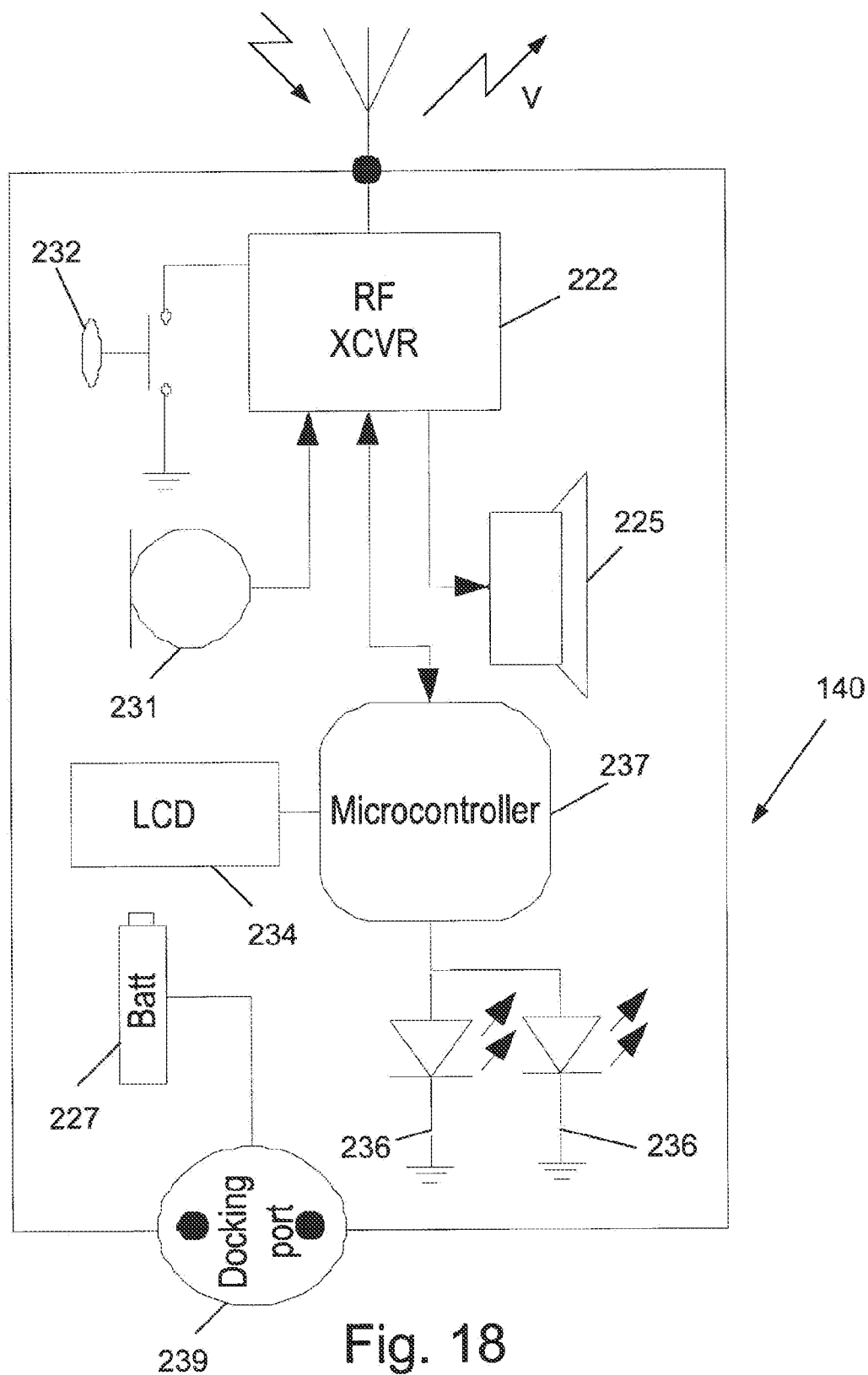
FIG. 18 is a block diagram of a portable unit, according to one embodiment of the invention.

FIG. 18 illustrates a block diagram of portable unit 140. Portable unit 140 comprises RF transceiver 222, speaker 225, and battery 227, e.g. a rechargeable battery, for powering portable unit 140. Battery 227 may be recharged by docking port 239, which may the same docking port used for the stationary unit or a separate charger. Transceiver 222 receives wireless signal $S_2$ when transmitted by the stationary unit. Wireless signal $S_2$ is then enunciated by means of speaker 225. Alternatively, portable unit 140 may comprise a cellular transceiver (not shown) for receiving a wireless signal via a cellular network.

Portable unit 140 may also comprise microphone 231 and Push-to-Talk (PTT) button 232. When the authorized attendant who is accessible to portable unit 140 desires to vocalize voice information, e.g. soothing words of comfort to an infant, PTT button 232 is depressed, and microphone 231 transmits the voice information to transceiver 222, which transmits the same as signal V to transceiver 206 (FIG. 17) of the stationary unit. The voice information is therefore able to be enunciated by speaker 202 (FIG. 17) of the stationary unit and heard by the infant.

In one embodiment, portable unit 140 also comprises microcontroller 237 and display 234, e.g. an LCD. A wireless status signal $S_2$ indicative of a subject related parameter of interest can be transmitted from the stationary unit to transceiver 222, which is subordinate to microcontroller 232. A relevant subject status can be displayed on alphanumeric display 234, or by means of optical indicators, e.g. LEDs.

Figure 19:
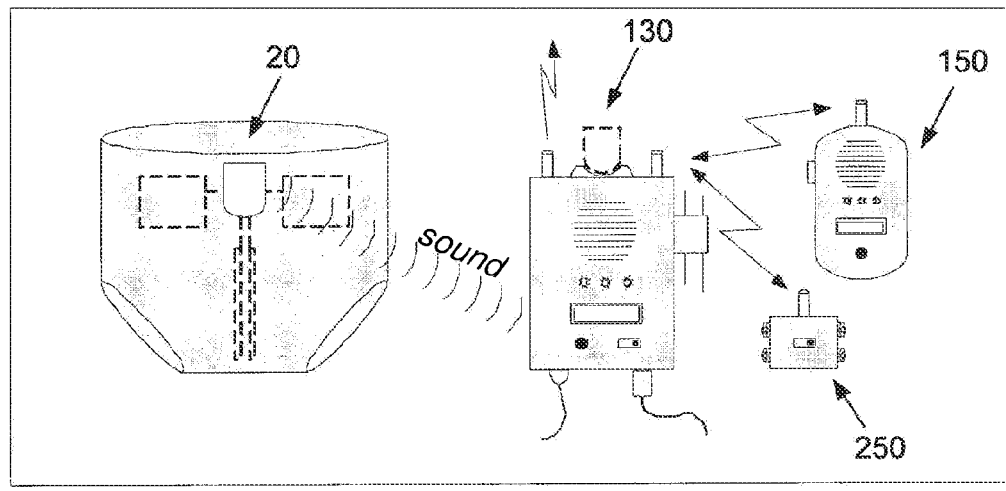
FIG. 19 is a schematic illustration of an infant monitoring system, according to another embodiment of the invention.

FIG. 19 illustrates another embodiment of a subject monitoring system, which is designated by numeral 240. In the example of FIG. 19, detector unit 20 is configured to emit a sound or audio signal (for example, of known or predetermined sound contact)—for example, detector unit 20 includes a speaker. The audio signal (i.e. 'alert signal' contingent upon a detected presence of a symptom of apnea or another detected condition of the subject) is then detected by a sound-detection unit (which may be stationary or portable—in FIG. 19 it is illustrated as 'stationary unit') that is deployed within audible range of the detector unit 20 (e.g. at least 2 meters or 5 meters or 10 meters and/or at most 100 meters or 20 meters or 10 meters). Sound detection unit 130 includes a microphone configured to detect sound and to generate an electrical signal descriptive of the detected sound. In addition, the system 240 may include electrical circuitry (i.e. including any combination of digital or analog electrical hardware and/or software/executable computer code—for example, including one or more microprocessors, volatile and/or non-volatile memory, and/or executable code stored in memory) configured to analyze the electrical signal descriptive of the detected sound and to determine if the electrical signal descriptive of the detected sound matches the pre-determined and/or known audio alert signal. This allows for distinction between ambient noise and other noise and noise specifically emitted by detection unit 20. This electrical circuitry maybe deployed in any location—for example, as part of unit 130 or in any other location.

System 240 may also include an alert signal-emitting unit (e.g. including a speaker or visual display or digital computer configured to sent an electronic communication) configured, in response to the results of the analysis by the electrical circuitry, and contingent upon a positive matching (i.e. a determination that the electrical signal descriptive of the detected sound from the microphone does match the sound characteristics of the audio alert signal), to emit one or more additional alert signals.

In some embodiments, the alert signal emitting unit and the sound detection unit are provided a a single unit 130 and co-reside in the same housing. It is appreciated that this is not a limitation, and other implementations are possible.

In one example, the additional alert signal is an additional audio alert signal. In another example, the additional alert signal may be visual alert signal. In yet another example, the additional alert signal may be provided by an electronic communication such as an email, a text message (e.g. an SMS), or a communication via a packet switched and/or internet network. In yet another example, the additional alert signal may be a radio signal or infra-red data communication.

System 240 may also include an additional portable unit 150 and/or override unit 250 in communication with alert signal-emitting unit 130

Figure 20:
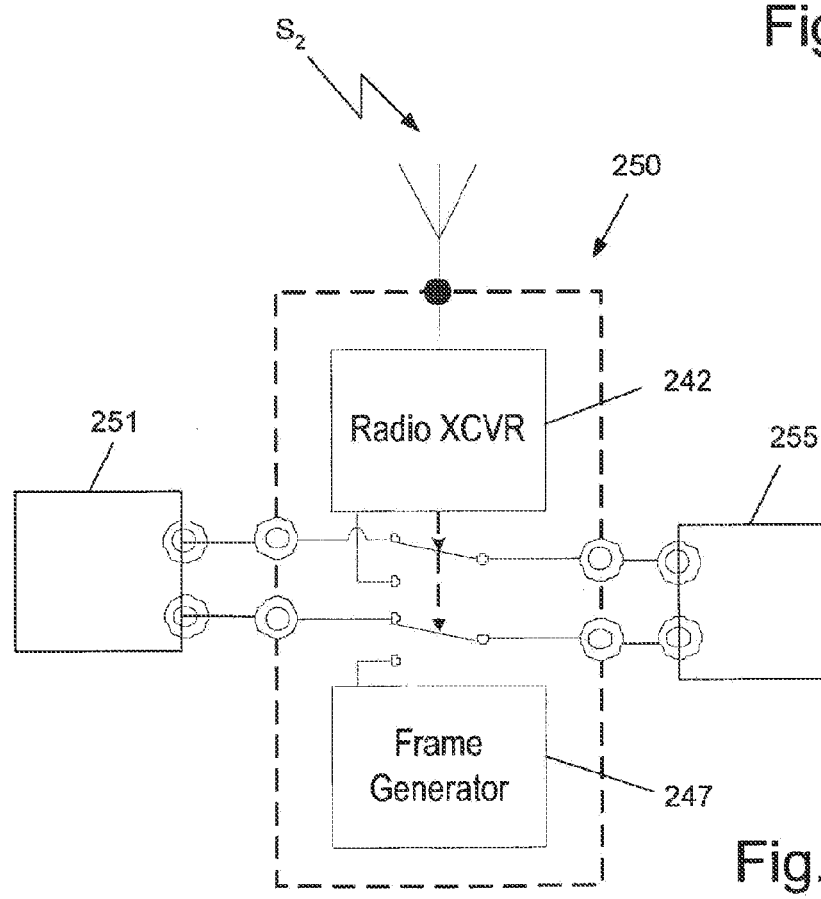
FIG. 20 is a block diagram of an override unit, according to one embodiment of the invention.

As shown in FIG. 20, override unit 250 comprises RF transceiver 242 and video frame generator 247. Override unit 250 is connected to set-top box 251, the function of which is well known to those skilled in the art and which is also connected to home entertainment system 255. When signal $S_2$ is received by transceiver 242, the display of a program via set-top box 251 and home entertainment system 255 is temporarily interrupted, whereupon a predetermined video frame is displayed on home entertainment system 255. When signal $S_2$ is a warning signal or is based on voice information vocalized by the infant, the voice information can be heard on home entertainment system 255. If so desired, override unit 250 may be used to actuate a home automation system, for activating a device to alert an authorized attendant.

While some embodiments of the invention have been described by way of illustration, it will be apparent that the invention can be carried out with many modifications, variations and adaptations, and with the use of numerous equivalents or alternative solutions that are within the scope of persons skilled in the art, without departing from the spirit of the invention or exceeding the scope of the claims.

What is claimed is:

1. A method of detecting apnea of a human subject using one or more capacitor plates, the method comprising at a time when at least one of the capacitor plates is mechanically coupled to an article of clothing worn by the human subject:
   a) capacitively sensing a distance(s) between:
      i) the mechanically coupled capacitor plate and;
      ii) an outer surface of the human subject's body, to generate a sensor-output electrical signal, said distance traversing a thickness of the article of clothing;
   b) analyzing time variations in the sensor-output electrical signal to determine if the time variations are indicative of a symptom of apnea in the subject; and
   c) generating an apnea alert signal that is contingent on the results of the apnea determining.

2. The method of claim 1 wherein the capacitance sensing occurs within a circuit comprising the following serially-connecting circuit elements:
   i) a first of the capacitor plates;
   ii) the subjects body; and
   iii) a second of the capacitor plates.

3. The method of claim 1 wherein there are at least two capacitor plates and each capacitor plate is coupled to the article of clothing such that the capacitor plates are next to each other separated by an insulating portion of the article of clothing.

4. The method of claim 1 wherein at least one of the capacitor plates is releasably attachable to the article of clothing.

5. The method of claim 1 wherein at least one of the capacitor plates is embedded within the article of clothing.

6. A system for detecting apnea of a human subject, the system comprising:
   a) an article of clothing wearable by the human subject; and
   b) a capacitance-sensor configured to capacitively sense a distance(s) between: i) at least one article of clothing associated capacitor plate that is mechanically coupled to the article of clothing and that is part of the capacitance sensor; and ii) an outer surface of the human subject's body when the article of clothing is worn by the human subject, thereby generating a capacitance output signal, said distance traversing a thickness of the article of clothing;
   c) a detector unit in communication with the at least one article of clothing coupled capacitor plate, the detector unit configured to analyze time variations of the capacitance output signal to determine if the time variations are indicative of a symptom of apnea in the human subject, and contingent on the results of the apnea determining, to generate an alert signal.

7. The system of claim 6, wherein the detector unit is configured to emit acoustical information, and further comprising a stationary unit disposed within an audible range of the detector unit, the stationary unit configured to receive the acoustical information and to send a wireless signal to a portable unit indicative of an apnea status of the subject.

8. The system of claim 6, wherein the article of clothing is a diaper.

9. The system of claim 6, wherein the capacitance-sensor is configured to capacitively sense the distance independent of any pressure exerted on the capacitance-sensor.

* * * * *